(12) United States Patent
Freudenthal

(10) Patent No.: US 9,179,899 B2
(45) Date of Patent: Nov. 10, 2015

(54) IMPLANTABLE DEVICE

(75) Inventor: Franz Freudenthal, La Paz (BO)

(73) Assignee: PFM MEDICAL AG, Cologne (DE)

( * ) Notice: Subject to any disclaimer, the term of this patent is extended or adjusted under 35 U.S.C. 154(b) by 1673 days.

(21) Appl. No.: 11/973,267

(22) Filed: Oct. 4, 2007

(65) Prior Publication Data

US 2008/0262518 A1    Oct. 23, 2008

Related U.S. Application Data

(60) Provisional application No. 60/853,128, filed on Oct. 20, 2006.

(30) Foreign Application Priority Data

Oct. 5, 2006 (DE) .......................... 10 2006 047 494

(51) Int. Cl.
*A61B 17/00* (2006.01)
*A61B 17/12* (2006.01)
(Continued)

(52) U.S. Cl.
CPC ....... *A61B 17/0057* (2013.01); *A61B 17/12022* (2013.01); *A61B 17/12031* (2013.01); *A61B 17/12036* (2013.01); *A61B 17/12109* (2013.01); *A61B 17/12113* (2013.01); *A61B 17/12118* (2013.01); *A61B 17/12122* (2013.01); *A61B 17/12172* (2013.01); *A61L 31/08* (2013.01); *A61B 19/54* (2013.01);
(Continued)

(58) Field of Classification Search
CPC ..................... A61B 17/0057; A61B 17/12031; A61B 17/12036; A61B 17/12122; A61B 17/12172; A61B 17/12022; A61B 2017/12054; A61B 2017/005875; A61B 2017/00592; A61B 2017/00597; A61B 2017/00606; A61B 2017/00615; A61B 2017/00601; A61B 2017/0061; A61B 2017/00628; A61B 2017/00632
USPC .......................................... 606/198, 200, 213
See application file for complete search history.

(56) References Cited

U.S. PATENT DOCUMENTS

| 3,786,816 A | 1/1974 | Wolvek |
| 5,108,420 A | 4/1992 | Marks |

(Continued)

FOREIGN PATENT DOCUMENTS

| CA | 2627196 | 5/2007 |
| DE | 28 22 603 | 11/1979 |

(Continued)

*Primary Examiner* — Dianne Dornbusch
(74) *Attorney, Agent, or Firm* — Grossman, Tucker, Perreault & Pfleger, PLLC

(57) ABSTRACT

In an implantable device (1) for use in the human and/or animal body for closure or partial closure of defect openings (2), cavities, organ passages etc or for providing a defined communicating opening between walls, organs, cavities etc comprising a carrier structure (17) which in a primary form has a large ratio of length to transverse extent along an axis (x) and in a secondary form has a smaller ratio of length to transverse extent along the axis (x), wherein the carrier structure (17) has a proximal and a distal portion (10, 11) and is formed in the manner of a weft and/or mesh and/or layered cloth and/or gauze, at least the one portion (11) in the secondary form has a first part (14) facing outwardly away from the other portion (10) or towards same and a second part (13) which deploys first from the primary form into the secondary form and which is folded back in a direction towards the other portion (10) or inwardly on to the first part (14).

58 Claims, 11 Drawing Sheets

Figure 14:
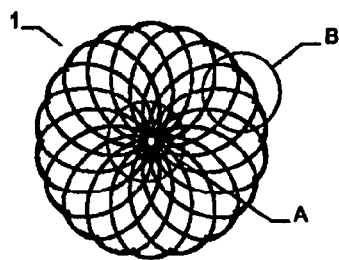

(51) Int. Cl.
*A61L 31/08* (2006.01)
*A61B 19/00* (2006.01)

(52) U.S. Cl.
CPC .............. *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/00628* (2013.01); *A61B 2017/00867* (2013.01); *A61B 2017/00893* (2013.01); *A61B 2017/12054* (2013.01)

(56) References Cited

U.S. PATENT DOCUMENTS

| | | | |
|---|---|---|---|
| 5,171,259 A | 12/1992 | Inoue | |
| 5,433,727 A | 7/1995 | Sideris | |
| 5,683,411 A * | 11/1997 | Kavteladze et al. | 606/200 |
| 5,725,552 A * | 3/1998 | Kotula et al. | 606/213 |
| 5,733,294 A * | 3/1998 | Forber et al. | 606/151 |
| 5,846,261 A * | 12/1998 | Kotula et al. | 606/213 |
| 5,976,174 A * | 11/1999 | Ruiz | 606/213 |
| 6,077,281 A | 6/2000 | Das | |
| 6,123,715 A | 9/2000 | Amplatz | |
| 6,149,665 A | 11/2000 | Gabbay | |
| 6,334,864 B1 * | 1/2002 | Amplatz et al. | 606/200 |
| 6,425,924 B1 * | 7/2002 | Rousseau | 623/23.64 |
| 6,468,303 B1 * | 10/2002 | Amplatz et al. | 623/1.2 |
| 6,506,204 B2 * | 1/2003 | Mazzocchi | 606/200 |
| 6,599,308 B2 * | 7/2003 | Amplatz | 606/200 |
| 6,719,781 B1 * | 4/2004 | Kim | 623/1.13 |
| 6,797,083 B2 * | 9/2004 | Peterson | 148/563 |
| 7,665,466 B2 * | 2/2010 | Figulla et al. | 128/830 |
| 7,727,189 B2 * | 6/2010 | VanTassel et al. | 604/104 |
| 7,757,692 B2 * | 7/2010 | Alferness et al. | 128/207.15 |
| 7,842,053 B2 * | 11/2010 | Chanduszko et al. | 606/157 |
| 8,100,938 B2 * | 1/2012 | Figulla et al. | 606/213 |
| 2003/0191495 A1 | 10/2003 | Ryan et al. | |
| 2004/0073155 A1 | 4/2004 | Laufer et al. | |
| 2004/0098095 A1 | 5/2004 | Burnside et al. | |
| 2005/0070992 A1 | 3/2005 | Bolduc et al. | |
| 2005/0137698 A1 | 6/2005 | Salahieh et al. | |
| 2005/0228434 A1 | 10/2005 | Amplatz et al. | |
| 2006/0058872 A1 | 3/2006 | Salahieh et al. | |
| 2006/0224183 A1 | 10/2006 | Freudenthal | |
| 2006/0235463 A1 | 10/2006 | Freudenthal et al. | |
| 2006/0247680 A1 * | 11/2006 | Amplatz et al. | 606/213 |
| 2007/0043391 A1 * | 2/2007 | Moszner et al. | 606/213 |
| 2007/0112380 A1 * | 5/2007 | Figulla et al. | 606/213 |
| 2008/0065146 A1 | 3/2008 | Mazzocchi et al. | |

FOREIGN PATENT DOCUMENTS

| | | |
|---|---|---|
| DE | 42 22 291 | 1/1994 |
| KR | 2001-0084836 | 9/2001 |
| WO | 97/28774 | 8/1997 |

\* cited by examiner

FIG. 1A
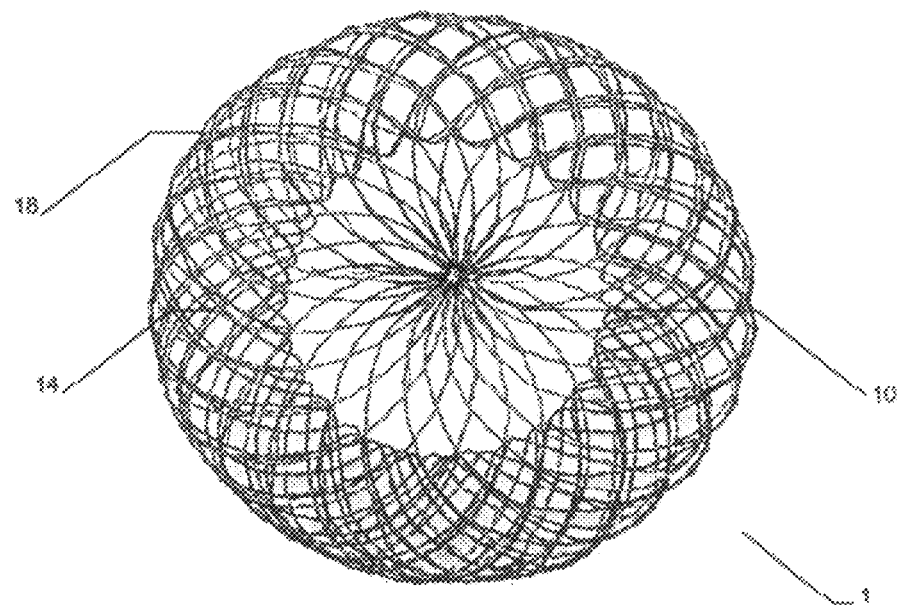
FIG. 1B
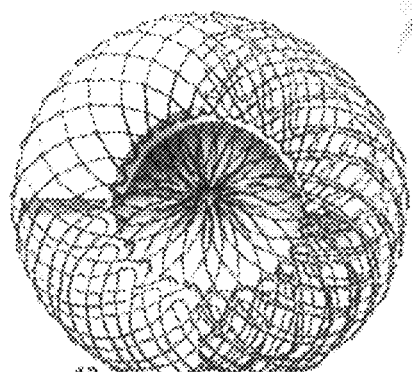
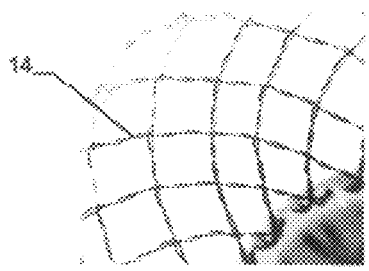
FIG. 1C
FIG. 1D
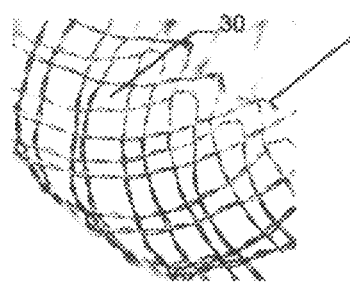
FIG. 1E
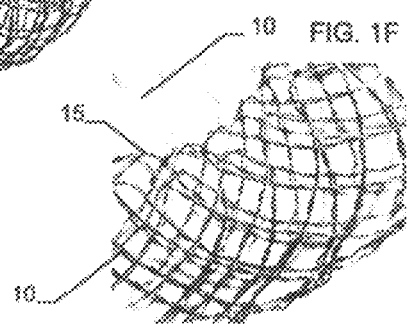
FIG. 1F

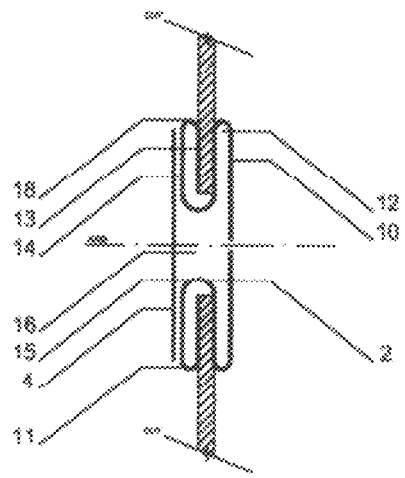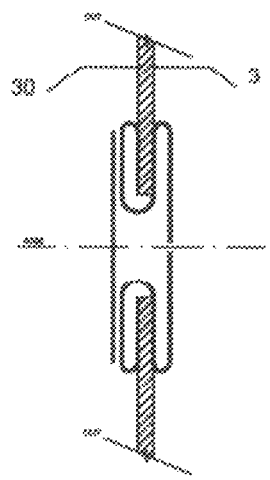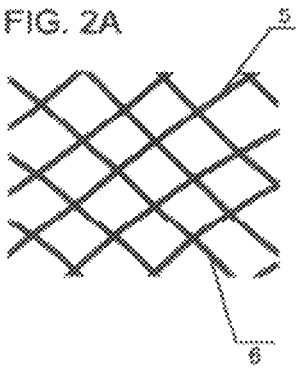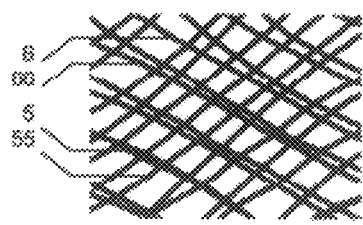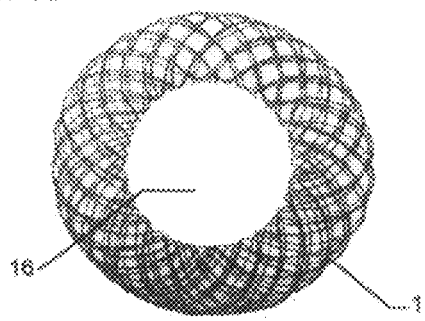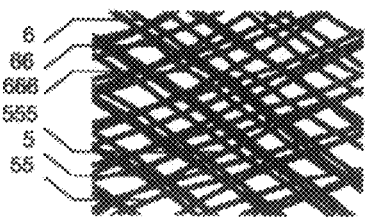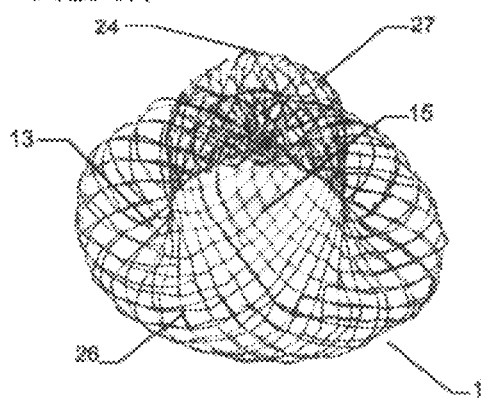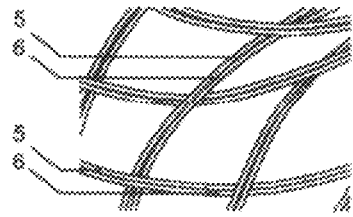

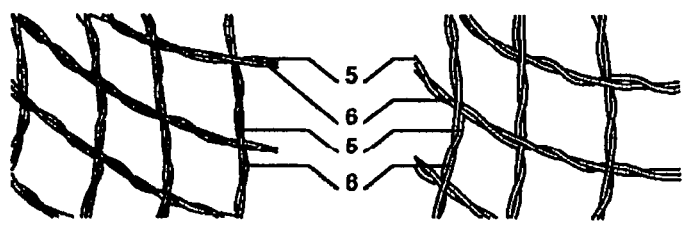
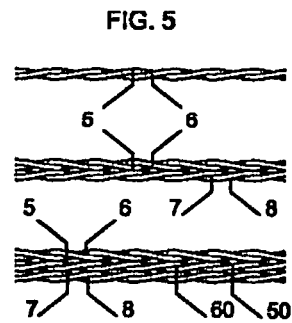
FIG. 3  FIG. 4  FIG. 5
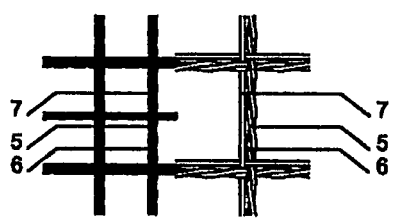
FIG. 6
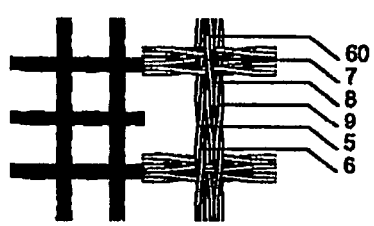
FIG. 9  FIG. 7  FIG. 11
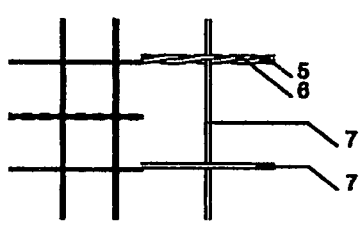
FIG. 12  FIG. 10  FIG. 13
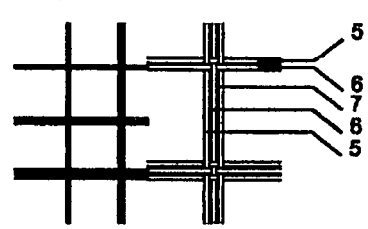

IMPLANTABLE DEVICE

This application claims the benefit of U.S. Provisional Application Ser. No. 60/853,128, filed Oct. 21, 2006, and incorporated herein in its entirety by reference, and German Patent Application No. 10 2006 047 494, filed Oct. 5, 2006, and also incorporated by reference herein.

The invention concerns an implantable device for use in the human and/or animal body for closure or partial closure of defect openings, cavities, organ passages etc or for providing a defined communicating opening between walls, organs, cavities etc comprising a carrier structure which in a primary form has a large ratio of length to transverse extent along an axis and in a secondary form has a smaller ratio of length to transverse extent along the axis, wherein the carrier structure has a proximal and a distal portion and is formed in the manner of a weft and/or mesh and/or layered cloth and/or gauze.

Implantable devices of that kind are known from the state of the art. By way of example DE 103 02 447 A1 discloses such an implantable device in which the proximal and/or the distal portion in the secondary form is of a substantially flat, disk-shaped or annular configuration and is bent away outwardly from an intermediate section connecting the distal or proximal portion, enclosing an internal space. Additional fibers or mesh portions which serve as a membrane element can be incorporated into the implantable devices. The provision of such membrane elements means that for example defect openings in the heart of a human being can be closed. Tissue can possibly grow on there.

DE 100 00 137 A1 also discloses such an implantable device for closing defect openings in the human or animal body, in which the secondary form assumes approximately the form of a double disk with a proximal disk element and a distal disk element for receiving the area around a defect opening between the disk elements. The carrier structure is substantially in one piece without joins, in which respect it is produced from a cut tube portion. Once again, a membrane can be provided within the implantable device, which membrane can be arranged at different sides of the implantable device or which can even be pulled like a sock with suitable openings for a placement system over the implantable device itself.

DE 103 38 702 B1 also discloses a corresponding implantable device in which a proximal and a distal retention region is provided with a cylindrical limb disposed therebetween, wherein the proximal retention region is of a form which is open towards the proximal end. The ends of the wires or threads of the distal retention region of the implantable device are held together with a holder. In addition a weave inlay for completely closing a shunt can be arranged in the cylindrical limb or in the proximal retention region.

Further implantable devices are also known for example from U.S. Pat. No. 5,846,162 and U.S. Pat. No. 5,725,552 which are both of a bell shape. WO 93/13712 also describes an implant for the closure of septum defects, which in the implanted condition assumes a double-cone or double-disk configuration, in which case the outer structures are formed from wire elements which are not directly connected together. They are braced with material sail portions, wherein the sail portions are sewn together at a radius corresponding to the defect to be closed. A disadvantage with that system is that the implant which is made up of a large number of component parts requires a high level of assembly complication and expenditure.

WO 95/27448 describes an implant which is used as a vein filter and which is to be used as a load-bearing structure for a septum closure. In that arrangement, a relatively elongate double cone is formed from a series of individual wires, while in an embodiment the cones are directed in relation to each other in the manner of a bone and in a further embodiment the cones are in the same direction, similarly to a fly agaric.

U.S. Pat. No. 5,433,727 A discloses an implant for closing large defects in the heart, such as for example an atrium-septum defect (ASD) or a ventricle-septum defect (VSD). In that case a kind of screen is placed in front of a septum defect and secured through the defect with a counterpart closure which is formed substantially from four loops each produced from a respective wire, which are deployed upon being ejected from the catheter and which are intended to prevent the implant slipping through to the side at the screen. The closure implant further includes a deployable foam resin disk which includes a coated wire skeleton in the form of an 'X', applied to the foam disk, as well as an adjustable loop, fitted to the center of the wire skeleton.

WO 97/28774 describes an implant which, upon being ejected from the catheter, is automatically deployed by virtue of a secondary form imparted thereto and which by elastic forces adapts itself to the dimensions of the defect in a wide range. The imparted structure is clamped in the manner of a double disk at both sides of the defect against the region surrounding the defect. The implant is formed from a series of wire elements which are joined together by suitable joining methods such as for example ultrasound welding or brazing. The implant is further provided with a covering which is fixed to the wire elements.

WO 99/12478 A1 also again discloses a corresponding implantable device in which there is provided a mesh comprising a plurality of interwoven Nitinol wires of a dumbbell or yo-yo shape. The implantable device, in its primary form, is in the form of a round mesh which at its two ends has loose wire ends which are subsequently each held in and welded in a sleeve. By virtue thereof the implantable devices formed each have projecting sleeves at their proximal and distal sides.

Further implants and catheter systems for the placement of such an implant are described for example in U.S. Pat. No. 5,108,420 A, DE 42 22 291 A1, DE 28 2 603 A, WO 96/01591 and EP 0 474 887 A1.

All the implantable devices described in the foregoing publications in the state of the art provide that defect openings can be admittedly closed to a better or lesser degree, particularly when they are provided with membrane elements. It will be noted however that all those implantable devices in the state of the art can be appropriately used only when there is sufficient space available for the deployment thereof at the respective implantation location. It is precisely in the region of the left atrium of the heart however that there is only very limited space available for implantation or for deployment of an implantable device.

Therefore the object of the present invention is to develop an implantable device as set forth in the classifying portion of claim 1, in such a way that it is also suitable for implantation at locations in the human and/or animal body, at which there is only a very small amount of space available for the implantation procedure, such as for example in the left atrium of a heart, wherein however the implantable device should also have particularly good stability in relation to unwanted displacement after the implantation procedure, and to provide a method of deploying the implantable device.

That object is attained by an implantable device as set forth in the classifying portion of claim 1 in that at least the one portion in the secondary form has a first part facing outwardly away from the other portion and a second part which deploys first from the primary form into the secondary form and which is folded back in a direction towards the other portion on to the first part.

The object is also attained by a method of deploying the implantable device from a primary form into a secondary form, in which a) the implantable device is arranged in an elongate primary form in a catheter, b) the implantable device is pushed out of the catheter in order to deploy into its secondary form with a low ratio of length to transverse extent, c) a part, which is pushed first out of the catheter, of a first portion of the implantable device is deployed and when a further part adjacent thereto of the portion of the implantable device is pushed out of the catheter is folded rearwardly in a direction towards the catheter, and d) the implantable device is completely deployed upon being further pushed out of the catheter. Further developments of the invention are defined in the appendant claims.

That thus provides an implantable device which requires only little space for implantation as, when the implantable device is pushed out of a corresponding catheter at the implantation location, it is usually only slightly pushed distally out of the catheter, the part which is pushed out first is folded over in the proximal direction, and, when the implantable device is further pushed out of the catheter, the part of the distal portion, which adjoins same and which is pushed out second and which faces distally is deployed. When the implantable device is further pushed out of the catheter, the part which is pushed out first is folded rearwardly on to the other part so that this affords a double-layer configuration for the two parts which are folded on to each other.

When the implantable device is arranged within a defect opening, for example in the wall of a heart, an intermediate portion which is advantageously provided between the proximal and the distal portions and which is of a reduced diameter in relation to the proximal and the distal portions passes through the defect opening or the wall, whereupon, when the implantable device is further pushed out of the catheter proximally from the defect opening or the wall, the proximal portion of the implantable device is deployed.

By virtue of the two parts of the one portion, in particular the distal portion, being folded back and folded on to each other, when the implantable device is pushed out of the catheter, only a small amount of space is required distally, which makes the implantable device according to the invention particularly suitable precisely for example implantation in the left atrium of a heart.

At least the one portion, in particular the proximal portion, is advantageously of a substantially disk-shaped or bulged configuration in its edge region. In principle, both portions can be of a similar configuration. Furthermore the one portion can be of a disk shape and the other can be of a bulged configuration. Advantageously the one portion has a carrier structure with a substantially closed end. In particular the carrier structure forms proximally a proximal end which is held together and which is arranged at the outside with respect to the implantable device. The substantially closed end can also be in the form of an end which is accommodated in a sleeve element and which holds together a weft and/or mesh and/or layered cloth and/or gauze end of the carrier structure. It can also be held together in some other fashion.

In the case of the implantable device for use in the human and/or animal body for the closure or partial closure of defect openings, cavities, organ passages etc, comprising a carrier structure which can be reproducibly converted from a primary form into an impressed secondary form, wherein the carrier structure has a proximal and a distal portion and is formed in the manner of a weft and/or mesh and/or layered cloth and/or gauze and wherein the one portion is of an outwardly opening form and the other portion is of a form which is closed in a bulging configuration and in particular closed by a sleeve element, the portion provided with the opened form advantageously has at least two parts which are folded on to each other.

If the proximal portion of the implantable device is of a substantially disk-shaped configuration, it can be particularly well applied for example to a wall which surrounds a defect opening, within which the implantable device is arranged. A bulge configuration in respect of the proximal portion can also guarantee a very good hold for the implantable device at the implantation location from the proximal direction, precisely when the implantable device is arranged at a slightly curved implantation location. When such a bulge configuration is provided, the proximal end of the implantable device is advantageously held together so that a through opening which is possibly provided through the implantable device can be kept as small as possible. That can form a closure means for an opening. In principle, it is also possible to provide a deliberate through opening through the implantable device here. If a closure effect is wanted, for example in addition the above-mentioned sleeve element can be fitted on to the proximal end, which is held together, of the implantable device.

By virtue of the double-layer configuration, which is folded back on to each other, of the distal portion, it is possible to achieve particularly good stability so that a particularly secure hold for the implantable device at the implantation location is possible. Deployment of the implantable device can be particularly critical precisely in the distal region which in particular is not easily proximally accessible as for example a so-called cobra effect can occur, in which the implant does not deploy properly but in the folded-together condition bends over at one side like the head of a cobra. It is particularly important here that the implantable device particularly reliably deploys in the desired shape. Intervention on the distal side of an implantation location is difficult in many situations as accessibility is afforded there only from a proximal direction, for example through a defect opening. Thus it has proven to be particularly advantageous that partial reinforcement of the implantable device on the distal side by virtue of the provision of the parts of the distal portion, which are folded on to each other, affords particularly good stability and thus a guarantee that the implantable device distally deploys in the proper fashion.

The double-layer configuration of the distal portion stabilises the implantable device at the edge, surrounding the implantation location such as for example a defect opening, and thus also provides assistance in regard to placement and fixing of the implantable device at the implantation location. The second part of the distal portion, which is folded back in a direction towards the proximal portion, is advantageously narrow in the form of a peripherally extending thin edge as that provides that an even shorter deployment length is required so that the space required upon deployment of the implantable device is even less. Alternatively or in part in addition, the second part of the distal portion, which is folded back in the direction towards the proximal portion, can extend to or to close to the intermediate portion between the proximal and the distal portions, and in particular can come to bear thereagainst. By virtue of that arrangement, stabilisation is possible, by virtue of the double-layer configuration of the distal portion, over the entire extent of the distally facing part of the distal portion. Furthermore the second part which for example bears against a wall in the heart of a human being or animal can bear resiliently thereagainst, either by the entire distal portion being of a slightly curved or arched configuration or at least the one part, in relation to the other part of the distal portion, being disposed one upon the other at a predeterminable or predetermined spacing so that such a spring action can be produced, which permits a particularly stable fit at the implantation location.

Advantageously the diameter of an intermediate portion which is provided between the proximal and the distal portions and which is of a diameter which is reduced in relation to the proximal and the distal portions and/or the diameter of a through opening extending through the implantable device is dimensioned in a predeterminable fashion, to provide the defined communicating opening between walls, organs, cavities in a human and/or animal body. The through opening through the implantable device or the intermediate portion between the distal and the proximal portions of the implantable device can therefore be of such a size that a desired defined communicating opening between two chambers, cavities, walls, organs etc in a human or animal body can be provided.

Advantageously the distal portion of the implantable device can deploy independently of the proximal portion thereof. In particular the distal portion can deploy completely and independently of the proximal portion. That makes it possible to also close relatively large defects, which is not possible for example with the implantable devices in the state of the art as, upon placement in the region of large defects in the heart of a human being or animal, they frequently slip off to the right side of the heart and thus do not produce their action.

At least one membrane element can be provided in the region of the proximal and/or distal portion and/or between the proximal or distal portions. The membrane element can be fixed to the weft, mesh, layered cloth or gauze of the carrier structure of the implantable device in a suitable fashion, for example by being sewn or glued there, or in some other fashion. Advantageously, the fixing between the membrane element and the carrier structure is provided by sewing in the region of the outer edge of the carrier structure. In particular fixing of the membrane element to the carrier structure is provided by passing a thread-like element around an edge of the membrane element and looping it around the edge side of the carrier structure and providing at least one knotting at an edge loop of the carrier structure. Sewing the membrane element and the carrier structure at the edge can not only provide a good secure fixing but can also provide that the carrier structure is completely covered by the membrane element without any problem, without the risk of the latter slipping.

It is further found to be advantageous if the dimensions of the membrane element approximately correspond to those of a defect opening to be closed. For example, by virtue of the at least double-layer configuration, which is directed rearwardly in the direction towards the proximal portion, of the distal portion, with two parts, it is possible for the membrane element to be fixed to the implantable device in such a way that it completely covers the left side of the heart in the region of a defect opening. The risk of clots which can form in the mesh of the carrier structure of the implantable device causing embolisms is minimal in that case, in contrast to the state of the art which uses a combination of polyester and Nitinol for the implantable device as the membrane element. In that case, polyester and Nitinol bear against each other in the region of the wall which surrounds a defect opening, which as a result can lead to clot formation which leads to the complications also described in specialist journals such as for example headaches or even temporarily blindness. Those complications advantageously no longer arise by virtue of the possibility that the membrane element in accordance with the invention is only of such a size as to correspond to the defect opening, when using an implantable device according to the invention.

It is further found to be advantageous for the membrane element to be fixed in the implantable device in such a way that the membrane element in the secondary form in the implantable device assumes approximately the dimension of a defect opening to be closed. In that way it is possible for the membrane element to be accurately fixed to the implantable device in such a way that it exactly assumes the same size as the respective hole to be closed or the defect opening to be closed. That makes it possible to advantageously use membrane elements which are as small as possible, which is advantageous precisely because the clotting risk is reduced, the smaller the size of the membrane element. In that way the edge surrounding a defect opening, for example of a wall in the heart of a human being or an animal, is surrounded exclusively by the mesh or gauze of the carrier structure of the implantable device and not by a combination of that mesh or gauze with the membrane element, whereby the clotting risk can be considerably reduced.

It is found to be particularly advantageous, as mentioned, if the membrane element is of such a size and is so fixed to the implantable device that in the secondary form of the implantable device the membrane element substantially completely covers it over and in particular substantially completely covers over the distal portion. A reduced risk of clotting is found to be an advantageous effect here. That is proven to be advantageous in particular on the left side of the heart as it is from there that the blood flows to the brain of a human being or animal so that clotting can have particularly threatening consequences. From the right side of the heart of a human being or animal the blood flows to the lungs where clots can be filtered and dissolved so that clotting does not have such adverse consequences there.

It will be appreciated that a plurality of membrane elements can also be used in an implantable device, which leads to a marked improvement in the closure options in respect of the implantable device in an opening to be closed. Furthermore the structure configuration (gauze, layered cloth, mesh, weft etc) of the carrier structure of the implantable device can be so dense that a membrane element is no longer required and the carrier structure of the implantable device itself takes over the function of such a membrane element. The structure configuration of the carrier structure of the implantable device is in that case so dense that the carrier structure acts as the membrane element.

The carrier structure of the implantable device can comprise for example a shape memory material, in particular a metal or a metal alloy, in particular Nitinol, or a plastic material. The membrane element if such is provided can comprise a plastic material, in particular polyester or another polymer. The carrier structure of the implantable device is advantageously formed from a single wire-like element. It can however also be formed from a plurality of wire-like elements. In that respect the carrier structure can be formed from a single, a double, or a double wound, a triple, a triple braided, wire-like element, in particular Nitinol wire, or a multiply wound, twisted or braided wire-like element, in particular Nitinol wire. In addition it is possible to provide combinations of the foregoing variants. It has proven to be particularly advantageous that, in such a configuration of the implantable device, the implantable device, upon being pushed out of a catheter, does not assume the cobra shape already referred to above, which in the case of systems in the state of the art of different configurations in respect of the structure forming them, leads to major problems precisely when dealing with large implantable devices.

The use of only one single wire-like element for affording the carrier structure (gauze, mesh, weft, layered cloth etc) of the implantable device means that no welded or soldered locations have to be provided as joining locations between individual wire-like elements, which has the result that there is scarcely any risk of corrosion and there is also no fear of fractures which can otherwise occur at such joining locations. Such corrosion and joining locations can otherwise lead to failure of the implantable device and even injuries to the patient or complications after implantation or in the case of fractures possibly also during the implantation procedure. Such problems encountered in the state of the art advantageously no longer occur with the implantable device according to the invention.

The at least one wire-like element can be of a round or flat cross-sectional shape or any combination of a flat and round cross-sectional shape. Furthermore the carrier structure of the implantable device can provide at the ends one or more loops or eyes. The loops or eyes, in the direction of the remaining part of the carrier structure, can go into a twisted or interwoven portion so that a greater degree of stability can be partially achieved with at the same time the provision of a less dense mesh or gauze. The ends of the one wire-like element are advantageously woven together in the surface of the carrier structure. By virtue of that arrangement, no wires which could injure blood vessels or tissue surrounding the implantation location project out of the carrier structure at the ends.

Advantageously the carrier structure of the implantable device includes twisted wire-like elements which are woven or braided to each other or portions, which are twisted together, of wire-like elements which at intersection points are braided individually or in the form of twisted elements through each other. The carrier structure of the implantable device as such can comprise one or more wire-like elements which are woven or braided together, wherein portions of wire-like elements can also be twisted together so that they can also be defined as a pair of elements. When wire-like pairs of elements which are twisted together are provided, the individual wire-like elements can each be individually braided through each other at the intersection points or the overall pair of elements can be braided through the other pair. In the latter variant the two wire-like elements or the two portions, which are twisted together, of the wire-like elements, surround the other pair of elements. In a corresponding fashion, thicker strands of wire-like elements or portions of wire-like elements can also be braided together. Twisting of the wire-like elements or portions thereof means that it is possible to ensure a higher level of stability while braiding of the twisted pairs of elements in the specified fashion means that the position of the individual pairs of elements in the carrier structure can be secured so that holes of different sizes cannot unintentionally occur in the carrier structure by a one-sided tension on the implantable device.

The carrier structure can be formed from at least one wire-like element in a single-layer, double-layer or multi-layer configuration. That can not only influence the stability of the carrier structure but naturally also the density thereof so that a defect opening can possibly be closed even without a membrane element.

The individual strata or layers of the carrier structure can comprise the same material or different materials. By way of example at least one of the layers can comprise Nitinol, at least one further layer can comprise polyester and at least one further layer can comprise PTFE. In that way it is possible to produce carrier structures with a desired degree of stability and possibly partially different levels of strength. Furthermore at least one membrane element can be arranged between at least two layers. The membrane element can be securely held fast between those layers of the carrier structure. Advantageously the choice of material for the membrane element can be matched to that of the individual layers of the carrier structure, between which it is arranged.

The implantable device can be of a concentric or eccentric shape. Advantageously the carrier structure of the implantable device can automatically adapt to the configuration involved at an implantation location, with the at least one part of the one portion, which in the secondary form is folded back in a direction towards the other portion. The particular configuration of the in particular distal portion of the implantable device, with the one part which is in a folded-back condition, provides that the implantable device or the carrier structure thereof does not have a fixed center so that the implantable device can flexibly adapt to any form of a defect or can already be adapted in respect of the secondary form imparted thereto. If for example the defect opening is one which is of an oval shape, the implantable device can also assume an oval shape, in which case it is a particularly good fit into the defect opening. Adaptation to adjacent walls against which the implantable device bears is also possible without any problem, in which respect the device provides for a particularly secure and firm hold at the implantation location by virtue of the folded-back part and thus the at least double-layer portion (for example the distal portion). It often happens that a defect opening to be closed is arranged adjacent to an aorta. The implantable device advantageously adapts without any problem in respect of its configuration to the configuration of the defect opening and the region surrounding same, that is to say the aorta wall, in any direction. In a corresponding fashion the implantable device can also adapt for example to a defect opening in the region of the pulmanalis, the wall of the atrial septum, the sinus coronarius, the lung veins and structures surrounding valve edges, in particular walls.

Alternatively the implantable device can be shaped to be adapted to the configuration at an implantation location. That already provides a distal and/or proximal portion which is adaptedly preshaped, in particular prebent or precurved, in the secondary form of the implantable device, so that the implantable device can already be deployed in the form suitable for the implantation location. That makes it possible in particular to avoid pressure against an aorta, beside which the implantable device is disposed. Such a pressure against an aorta can otherwise lead to perforation thereof, which would have life-threatening consequences for a patient. The possibility of being able to provide for optimum adaptation of the implantable device to the configuration of the implantation location and to impart that shape to the device as its secondary form when advantageously using a carrier structure consisting of a shape memory material by virtue of heat treatment is further assisted by the portion which includes the part that is folded back or rearwardly and which as a result is at least of a double-layer configuration as that provides that the imparted secondary configuration is particularly stable. The risk that that specific configuration could be lost can be substantially excluded by virtue thereof. The possibility of pre-imparting a given secondary configuration which can be adapted even to worst-case situations in the region of a defect opening to be closed provides that now the patients which hitherto could not be treated by virtue of the danger of aorta damage can now also be treated. In the case of more than 30% of all ASD patients, no treatment can be implemented with the implantable devices hitherto available on the market as the risk of damage to the aorta wall or another wall or structure adjoining a defect opening is too great. As now advantageously the secondary form of the implantable device can be adapted to the conditions at the implantation location the risk of pressing in or damaging the aorta wall or another wall or structure adjoining the defect opening to be closed no longer arises so that those patients can now be treated. By virtue of the at least double-layer part of the one portion the configuration of the implantable device, which is adapted to the implantation location, is not lost but rather remains stable.

Advantageously at least one element is provided as a marker for visually indicating the implantable device under a monitoring device during an implantation operation. The at least one element can be a microspiral provided at the edge on the implantable device. Such a microspiral can be wound portion-wise around the implantable device at the edge thereof. Particularly preferably the at least one element comprises an X-ray-visible material, in particular a material containing between 70 and 90% platinum and between 30 and 10% iridium. It will be appreciated that it is also possible to use other materials which also allow the device to be visually indicated under a monitoring device.

By virtue of the particular configuration of the implantable device according to the invention it is MNR-compatible and thus does not give rise to problems in terms of monitoring an implantation operation. The implantable device can thus be tracked during the implantation procedure in particular by imaging processes such as for example X-ray representation, echography, cintigraphy etc. If, as in the state of the art, there are weld locations on high-quality steel wires, artefacts are produced when using imaging processes, and such artefacts lead to problems in terms of tracking the implantation procedure.

Such an implantable device according to the invention can be placed in a defect opening with a suitable ejection system at any angle, in which respect the implantable device can then be appropriately adapted to the implantation location or oriented there and securely placed. The ejection system according to the invention is so designed that the implantable device can be rotated therewith, in particular by actuation by holding wires with respect to a guide or ejection wire. Advantageously the ejection wire has a very thin tip of a diameter of between about 0.1 and 0.3 mm. That makes it easily possible for it to be threaded through the carrier structure of the implantable device, even if the latter is of a very close-mesh nature. The holding wire has at least one loop for passing the ejection wire therethrough. Advantageously for fixing to the implantable device the holding wire can be threaded through end loops of the carrier structure of the implantable device. That makes it possible to provide for a particularly firm hold on the carrier structure of the implantable device in order to be able to hold and direct it in the implantation procedure. Alternatively or additionally the holding wire can be threaded through a carrier ring connecting end loops of the implantable device together.

Advantageously the implantable device can be rotated and floated around the at least one ejection wire and the at least one holding wire. That permits exact positioning even at locations which involve difficult access, in a human or animal body.

In a method of ejecting an implantable device at an implantation location in a human or animal body using such an ejection system at least one holding wire is threaded through loops arranged at the end on a carrier structure of the implantable device and/or a carrier ring connecting loops arranged at the end on a carrier structure of the implantable device and an end loop is formed on the holding wire. In addition an ejection wire is threaded through the end loop of the holding wire and the implantable device and the holding wire is thereby fixed to the ejection wire. Subsequently the ejection wire together with the implantable device is advanced through a catheter along the ejection wire together with the holding wire to the implantation location and the implantable device is deployed there. For ejection of the implantable device the ejection wire is pulled back in the proximal direction and pulled out of the end loop of the holding wire, and the holding wire is pulled out of the loops of the implantable device and pulled back through the catheter. In that case the ejection wire and the holding wire to facilitate the advance movement can be arranged in a sheathing element within the catheter.

By virtue of the possibility of rotating the implantable device with the ejection system holes or defect openings of very different configurations can be exactly closed. Therefore, even when the implantable device is of an eccentric configuration, precise placement is possible by virtue of the rotational capability afforded with the ejection system, in which respect such eccentricity is found to be advantageous precisely when only little space is available at one side, as for example in the region adjacent to an aorta or other boundary configurations, for example walls in the heart of a human being or animal.

With the advantageously provided very thin tip of the guide or ejection wire, of a diameter of in particular between 0.1 and 0.3 mm, flotation of an implantable device with the ejection wire is possible. If the position of the implantable device is not satisfactory the implantable device can still be removed through the catheter in spite of free flotation. If in contrast the position adopted by the implantable device is satisfactory it can be ejected from the catheter with the ejection system without modifying that good position of the implantable device. That is not possible with the ejection systems for implantable devices in the state of the art.

Although it has been described hereinbefore that the distal portion is advantageously of a double-layer configuration with two parts which are folded on to each other, it will be appreciated that it is basically possible for both portions, the proximal portion and the distal portion, to be designed in that fashion. Equally it is possible for the portion provided with the two parts which are folded on to each other in a corresponding fashion to be arranged as the proximal portion.

In addition the implantable device for use in the human or animal body for the closure or partial closure of defect openings, cavities, organ passages etc or for providing a defined communicating opening between walls, organs, cavities etc, can be provided with a carrier structure which is of an elongate primary form and a secondary form which is shorter in relation thereto, wherein the carrier structure has a proximal and a distal portion and is formed in the manner of a mesh and/or layered cloth and/or gauze, wherein the at least one portion of the carrier structure is wound up helix-like. It is also possible for both portions of the carrier structure to be wound up helix-like. The fact that the portion is wound up helix-like provides that the carrier structure in that portion becomes even more stable than when there is only a double-layer configuration present there by virtue of two parts of the portion being folded on to each other. The portion which is configured in the secondary form automatically in the form of a helix or a spiral arranged in transverse relationship with respect to the longitudinal extent of the implantable device is moreover obviously also more stable than a spiral which is otherwise known in the state of the art and which is formed from a wire-like element, in particular also by virtue of the provision of a carrier structure in the form of a gauze, mesh, weft, layered cloth etc. Furthermore the implantable device can be particularly easily introduced into a thin catheter and pushed out of same again. By virtue of the repeated rearward deployment which leads to the helix form, the secondary form of the implantable device can be of very large dimensions.

Advantageously the at least one portion which is wound up helix-like has a plurality of parts which face towards the respective other portion and a plurality of parts which face away from the other portion. The number of those parts, which are folded on to each other, of the helix-like portion can be selected to be any number. By way of example, it is possible to provide two parts which face towards the other portion and two parts which face away from that portion. The stability of the helix-like portion can be determined by the choice of the number of parts.

The other portion can be of the same configuration as or of a different configuration from the portion which is wound up in a helix-like configuration. In particular both portions can be folded up in a helix-like configuration, in which case the one portion can also be folded up less severely than the other portion.

If the arrangement does not have both portions folded up in a helix-like configuration, the portion which is not folded up in a helix-like configuration can be substantially flat and/or at least partially bulging and/or can be of a curved configuration. When the configuration involved is a flat configuration, the portion can be for example disk-shaped or can be in the form of a straight termination of a for example cylindrical intermediate portion between the two portions. An at least partial bulging configuration can also be combined with a curved shape. Conversely, a curved configuration can otherwise be substantially disk-shaped. The two portions can also be of differing diameters.

The portion which is folded in a helix-like configuration is generally provided with a through opening. The other portion can either also be provided with a through opening or can be substantially closed. In principle a sleeve element can also be fitted on to an end which is held together, that is to say of a closed configuration, if that is found to be advantageous in a use-specific situation.

In addition, at least one membrane element can be introduced into or secured to the at least one portion which is folded helix-like and/or the other portion. In principle it is also possible for both portions to be folded one upon the other in a helix-like configuration and for membrane elements to be provided in or on one or both portions.

Furthermore the implantable device for use in the human or animal body for the closure or partial closure of defect openings, cavities, organ passages etc or for providing a defined communicating opening between walls, organs, cavities etc can be provided with a carrier structure which is of an elongate primary form and a secondary form which is shorter in relation thereto, wherein the carrier structure has a proximal and a distal portion and is formed in the manner of a mesh and/or layered cloth and/or gauze, wherein at least the one portion in the secondary form includes two parts of which the one is deployed first from the primary form into the secondary form and is folded in a direction away from the other portion on to the second part which is directed towards said other portion. In that case the part which is folded over is advantageously folded back inwardly into the implantable device. That also provides for stabilisation of the one portion or in particular the edge thereof, by virtue of the part which is folded over. In comparison with folding the one part back outwardly, as described hereinbefore, a part which is folded inwardly cannot be folded back into the primary form, or at least can scarcely be folded back into the primary form again, if the implantable device is possibly to be pulled into a catheter again, after it has been deployed. Removal of the implantable device once ejected from the implantation location is therefore found to be difficult with this embodiment.

When using the inward folding of the one part straight long layered cloths or gauzes of the carrier structure can be particularly well reinforced at the end. In that respect production by machine is particularly suitable as manufacture can be implemented with that straight long structure more easily than by hand. Shorter implantable devices of a very complex configuration in contrast can be at least more effectively produced by hand.

The implantable device according to the invention can be particularly advantageously used for closing an atrium-septum defect (ASD), a ventricle-septum defect (VSD), a persistent foramen ovale (PFO), a congenital atrial defect of the heart and in persistent ductus arteriosus Botalli (PDA).

For use of the implantable device in relation to a persistent ductus arteriosus, it is found to be advantageous for the implantable device to be of a hat-shaped configuration with at least one double-layer hat brim-shaped portion. That hat shape provides that the head part-shaped portion of the implantable device can be introduced into the persistent ductus arteriosus for closure thereof. The hat brim-shaped portion bears against the aorta wall so that the aorta remains free.

It is further found to be advantageous if the double-layer hat brim-shaped portion is in the form of a portion having at least two parts which are folded on to each other. By virtue of that arrangement that portion, for being supported against the aorta wall, is of particular stability so that a particularly more secure seat is possible. Preferably the hat brim-shaped portion which bears against the aorta wall is shaped to correspond to the curvature of the aorta so that it can be particularly well attached thereto. In addition however, by virtue of the parts which are folded on to each other of the hat brim-shaped portion, it is possible for that portion to be automatically adapted to the configuration of the aorta and to be securely held fast there. By virtue of the parts of the portion, which are folded back or rearwardly on to each other, and the remaining configuration in the form of a hat, it is possible for holes of very greatly differing diameters to be closed by one and the same implantable device. By way of example a hole of a diameter of 8 mm can be sealingly closed with the same hat-shaped implantable device as a hole of a diameter of less than 3 mm. The flexibility of use of such a hat-shaped implantable device is therefore very high and likewise the specific configuration of the hat shape.

The head part-shaped portion of the implantable device, which is in opposite relationship to the hat brim-shaped portion, can be turned over in particular inwardly into the interior of the implantable device. By virtue thereof that portion can be closed and can be formed without an outwardly projecting end so that it is not only easier for the shape of the portion to be maintained stable but also no possibly injurious ends project out of the implantable device at that end.

In an advantageous feature, in the method according to the invention for the deployment of the implantable device, the part which folds rearwardly in a direction towards the catheter can be folded substantially flat on to the other part. In addition, as already mentioned, the part which folds rearwardly in a direction towards the catheter can be wrapped helix-like around itself. The configuration of the other above-mentioned shapes in respect of the implantable device can also be deployed as secondary forms when the implantable device is pushed out of the catheter.

It is found to be particularly advantageous if at least one of the surfaces of the implantable device, in particular of the carrier structure and/or the membrane element, is treated or coated with at least one functional material. By virtue thereof, in particular the effectiveness of the implantable device can be still further improved as on the one hand adverse reactions on the part of the body to the implantable device are avoided while on the other hand the region surrounding the implantation location can be treated directly by medication. In particular the functional material used for coating or treating the material used for the implantable device or the surfaces of the implantable device can be selected from the group consisting of inorganic materials, ceramic materials, synthetic polymers, human biopolymers, medication coatings, medication-liberating polymers, biomolecules, functional groups and genetic materials. In that respect one or more materials can be used and combined together, in particular to obtain a combination of various effects or functions.

Particularly preferably the functional material is selected from the group consisting of gold, biogold, diamond-like carbon (DLC), diamond-like nanocomposite (DLN), iridium oxide, nanoporous $Al_2O_3$, silicon carbide, hydroxylapatite, titanium nitrite oxide, poly(2-chloro-p-xylylene), polybutylmethacrylate, phosphorylcholine, polyethylene, polyethylene vinylacetate, polyhexymethacrylate, poly[bis](trifluoroethoxy)phosphazene, polytetrafluoroethylene, polyurethane, collagen, chondroitin sulfate, elastin, fibrin, hydraluronic acid, abciximab, heparin, paclitaxel, abciximab-liberating cellulose, angiopeptin-liberating phosphorylcholine, DNA-liberating polyethylene vinylacetate or polybutylmethacrylate, a medicament-liberating poly(L-lactide), paclitaxel or hirudin or iloprost-liberating polylactide, viral vector-liberating polylactide-phosphorylcholine, forskolin-liberating polyurethane and stem cells. In that respect for example surface passivation or an anti-oxidative coating can be provided by iridium oxide. Polyurethane can be applied for example in the form of a thin layer. Functionalised surfaces with biomolecules and functional groups can further be provided in the context of what is referred to as molecular surface engineering, that is to say the formation of molecular material surfaces by the introduction of functional groups. In addition the surfaces of the implantable device can for example be deliberately provided with cell ligand structures for adhesion of progenitor cells circulating in the blood. Poly(L-lactide) can be combined with a multiplicity of medications, in particular medications from the group of cystostatics, in which respect it is possible to use any kind of medication which leads to a respectively desired therapy outcome. For closing for example a congenital defect in the heart of a patient or a congenital cardiac flaw such as a PDA the substances or medications which can be combined with the polymers can be in particular substances for accelerating endothelisation, that is to say growth with body-specific cells.

The surface treatment of the implantable device can be implemented by using various processes such as for example a plasma treatment, especially in the application of DLC (diamond-like carbon) or DLN (a diamond-like nanocomposite), a PVD (physical vapor deposition) process, a CVD (chemical vapor deposition) process, ion implantation, sputtering, an ion beam process, a laser process, a thermal process, spin coating, dip coating and electropolishing.

Figure 15:
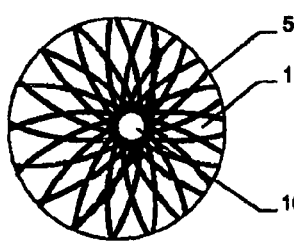
Figure 16:
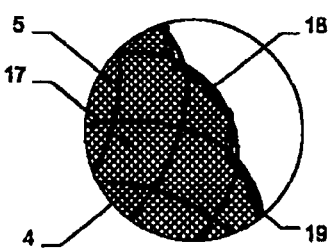
Figure 17:
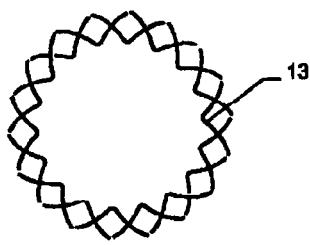
Figure 18:
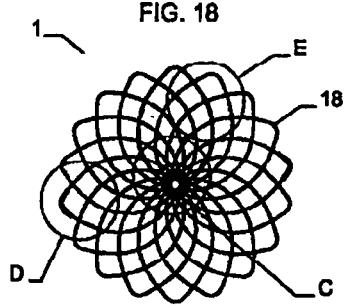
Figure 19:
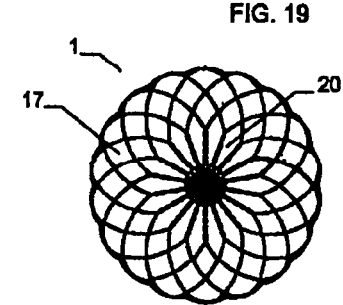
Figure 20:
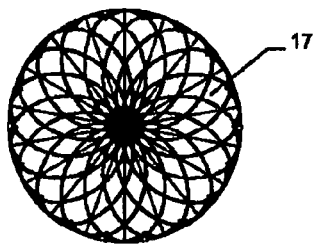
Figure 22:
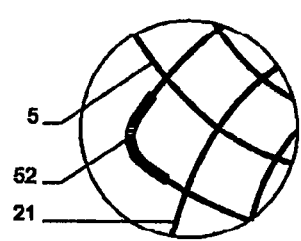
Figure 23:
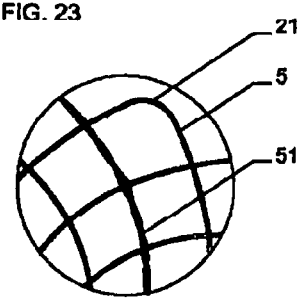
Figure 24A:
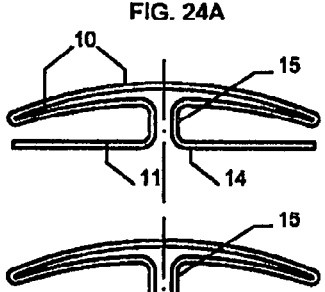
Figure 24B:
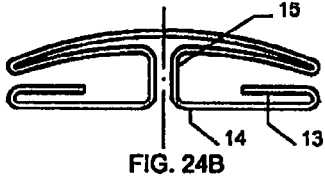
Figure 58:
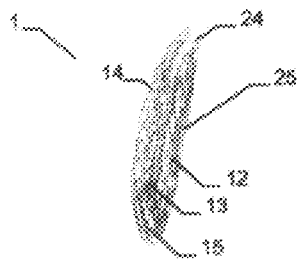
Figure 59:
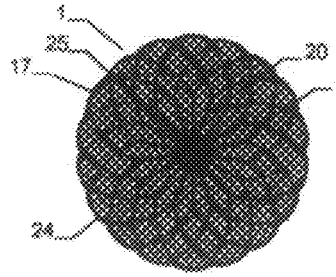
Figure 60:
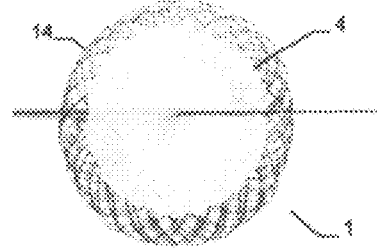
Figure 61:
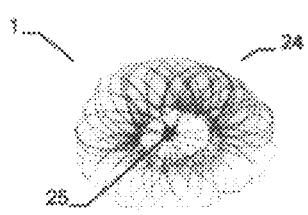
Figure 62:
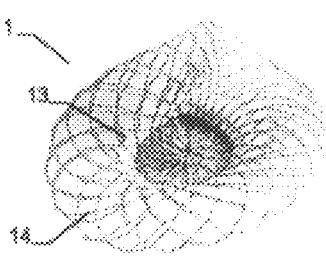
Figure 63:
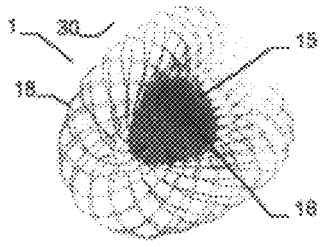
Figure 63:
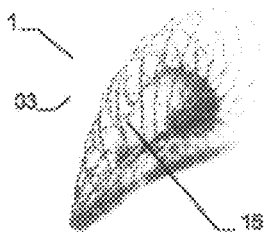
Figure 64:
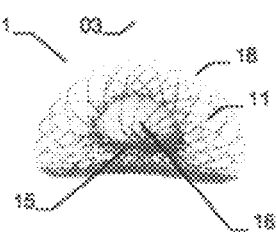
Figure 65:
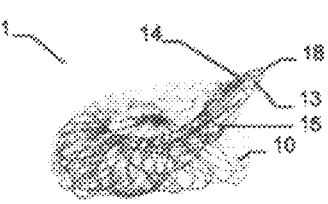
Figure 66:
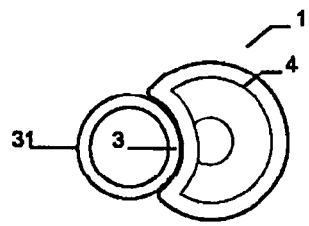
Figure 67:
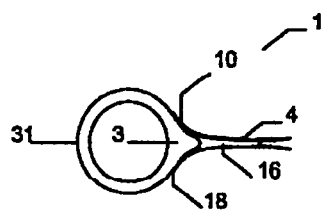
Figure 68:
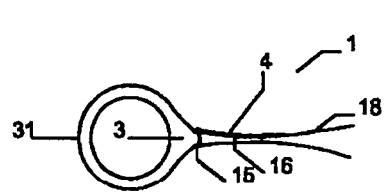
Figure 73:
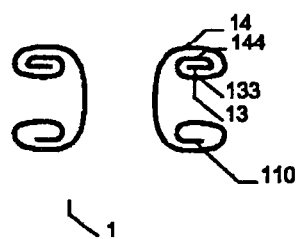
Figure 74:
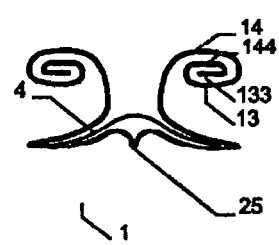
Figure 75:
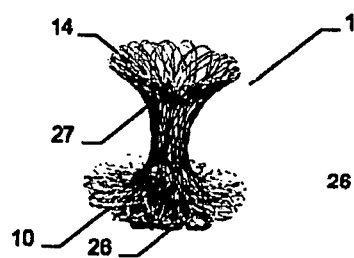
Figure 76:
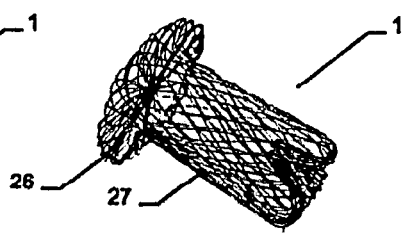
Figure 77:
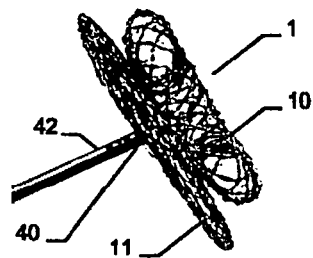
Figure 78:
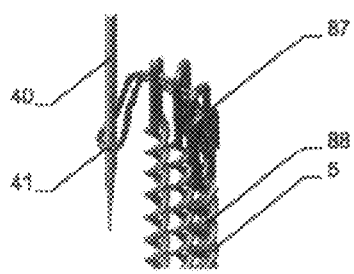
Figure 79:
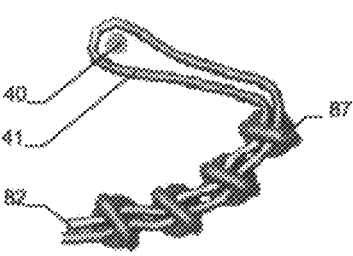
Figure 80:
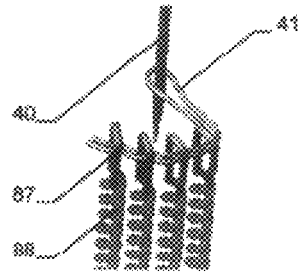
Figure 81:
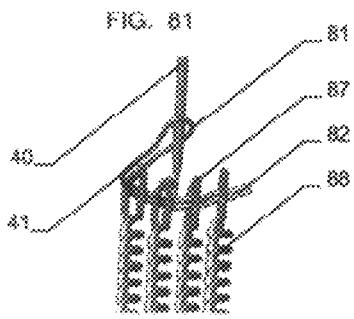
Figure 82:
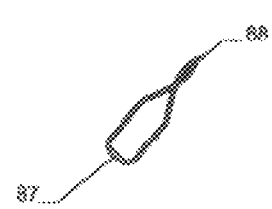
Figure 84:
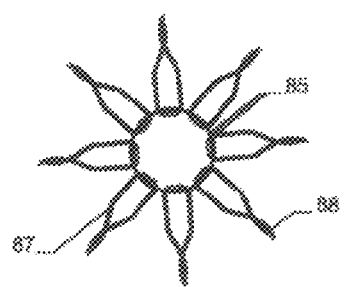
Figure 85:
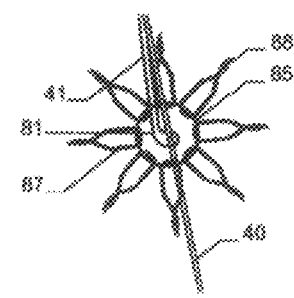
Figure 86:
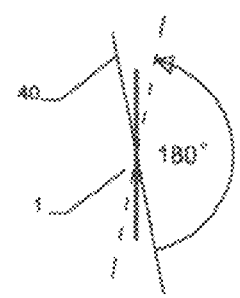
Figure 87:
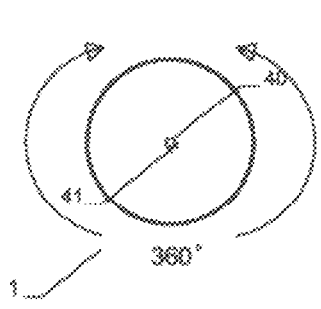
Figure 88:
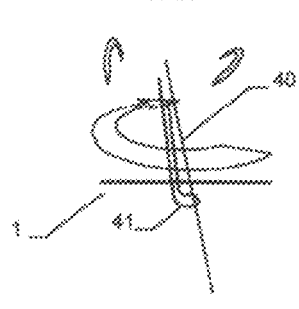
Figure 89:
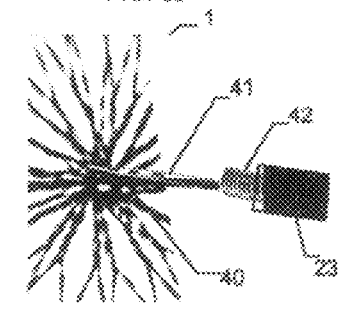

In order to describe the invention in greater detail embodiments by way of example thereof are set forth in fuller detail hereinafter with reference to the drawings in which:

FIG. 1A shows a plan view of a first embodiment of an implantable device according to the invention, FIG. 1B shows a plan view of a second embodiment of an implantable device according to the invention, FIGS. 1C through 1F show detail views of the implantable device of FIG. 1B, FIGS. 1G and 1H show diagrammatic side views in section through a wall in which the implantable device of FIG. 1A is arranged, FIG. 1J shows a plan view of a third embodiment of an implantable device according to the invention with a large-format through opening, FIG. 1K shows a perspective of a fourth embodiment of a hat-shaped implantable device according to the invention, FIGS. 2A through 2C show detail views of a single-layer, two-layer and a three-layer structural configuration of the carrier structure of an implantable device according to the invention, FIGS. 2D, 3 and 4 show a detail view of a single-layer structural configuration of the carrier structure of an implantable device according to the invention with interwoven pairs of elements, FIGS. 5 through 13 show detail view of various kinds of braiding for forming the carrier structure of an implantable device according to the invention, FIGS. 14 through 16 show a plan view of a further embodiment of an implantable device according to the invention and detail views of the central region and an edge region thereof, FIG. 17 shows a detail view of a rearwardly folded portion, FIGS. 18, 21, 22 and 23 show a plan view of a further embodiment of an implantable device according to the invention and detail views of the central region and two edge regions thereof, FIGS. 19 and 20 show a plan view on a front side and a rear side of a further embodiment of an implantable device according to the invention, FIGS. 24A and 24B show diagrammatic side views of further embodiments of an implantable device according to the invention, FIGS. 25 through 29 show a plan view of a further embodiment of an implantable device according to the invention and detail views of the central region, two edge regions and a region arranged therebetween, FIGS. 30 through 34 show side views of various possibilities of an arrangement of a membrane element in an implantable device according to the invention, FIGS. 35 through 42B show diagrammatic side views in principle of a catheter with an implantable device according to the invention during an ejection procedure for the implantable device at an implantation location, FIGS. 43 through 58 show perspective views of an ejection procedure for an implantable device according to the invention from a catheter, FIG. 59 shows a plan view of an embodiment of an implantable device according to the invention with a membrane element, FIG. 60 shows a plan view of a further embodiment of an implantable device according to the invention with another arrangement of a membrane element, FIGS. 61 through 64 show perspective views of implantable devices according to the invention which are adapted to an implantation location, FIG. 65 shows a perspective view of a further embodiment of an implantable device according to the invention which is shaped in such a way as to be adapted to an implantation location, FIG. 66 shows a diagrammatic plan view of an aorta and an implantable device according to the invention arranged at the aorta, FIGS. 67 and 68 show diagrammatic side views of implantable devices according to the invention arranged beside an aorta, FIGS. 69 through 74 show diagrammatic views in section of further embodiments of implantable devices according to the invention with portions which are folded rearwardly a plurality of times in a helix-like configuration, FIG. 75 shows a perspective view of a further embodiment of an implantable device according to the invention in the form of a hat with a protruding, hat brim-like portion and a protruding portion arranged in opposite relationship thereto, FIG. 76 shows a perspective view of a further embodiment of a hat-shaped implantable device according to the invention with a substantially cylindrical head part portion, FIG. 77 shows a perspective view of an implantable device according to the invention with a disk-shaped portion and a bulging portion, applied to an ejection wire, FIGS. 78 through 81 show perspective views of threading end loops of an implantable device according to the invention on to an ejection system according to the invention, FIG. 82 shows a plan view of an end loop as shown in FIG. 78, FIGS. 83 through 85 show plan views of end loops of an implantable device according to the invention, FIGS. 86 through 88 show diagrammatic views in principle showing the positioning of an ejection system according to the invention for an implantable device, FIG. 89 shows a perspective diagrammatic view in principle of an implantable device according to the invention provided with an ejection system in the form of a holding wire and an ejection wire, and FIGS. 90 through 101 show perspective views illustrating a further embodiment of an implantable device according to the invention being pushed out of a catheter.

FIG. 1A shows a plan view of an implantable device 1. As can be better seen from the side views of the implantable device in FIGS. 1G and 1H in which the implantable device 1 is disposed in an opening 2 in a wall 3, for example of a heart of a human being or an animal, in which respect FIGS. 1G and 1H only differ in that, for the sake of improved clarity, the references concerning the wall 3 are shown in FIG. 1H, the implantable device has a proximal portion 10 and a distal portion 11. The proximal portion 10 is shaped to surround an internal space 12 whereas the distal portion 11 is formed in a double-layer configuration by virtue of two parts 13, 14 which are folded on to each other. The one part 13 is bent back in a direction towards the proximal portion 10 and bears against the outside 30 of the wall 3 whereas the other part 14 is arranged distally at the outside and is connected to an intermediate portion 15 which interconnects the proximal and the distal portions 10, 11 and is arranged in the opening 2 in the wall 3. A membrane element 4 is also mounted on the outside on the distal part 14. The membrane element closes an opening 16 which is delimited on the inside by the part 14 and which passes through the intermediate portion. That provides that the distal portion 11 is also closed in the distal direction, like the proximal portion which is already that, by virtue of its substantially closed configuration.

The implantable device 1 is made up of a carrier structure which can be particularly clearly seen in FIG. 1A as well as in FIGS. 1B through 1F. It can be of the most widely varying configurations and for example can be in the form of a gauze, weft, layered cloth or mesh. FIG. 1B shows an implantable device 1 with four different carrier structure configurational designs. The configuration shown as a detail in FIG. 1C in the top left corner in FIG. 1B presents a single-layer carrier structure in the form of a mesh. It is formed by weaving two respective mutually twisted wire-like elements 5, 6. The structure shown in FIG. 1E is a two-layer structure, also formed by weaving two mutually twisted wire-like elements 5, 6. The structure shown in FIG. 1D is a three-layer structure and that shown in FIG. 1F is a four-layer structure, both also formed by weaving two mutually twisted wire-like elements 5, 6. The embodiment shown in FIG. 1A of the implantable device involves a four-layer carrier structure so that it is particularly dense in the region of the two parts 13, 14 which are folded on to each other. A peripherally extending outer edge 18 of the implantable device is of a uniformly curved configuration in the embodiments of FIGS. 1A through 1F.

FIG. 1J shows a further embodiment of an implantable device 1 in which, unlike the embodiments of FIGS. 1A through 1H, there is a large through opening 16 through the implantable device. With such a large through opening, it is possible for example to provide a defined through opening in the event of partial closure of a wall or an organ passage.

FIG. 1K shows an embodiment of an implantable device 1 which is designed in particular for use in a treatment of a persistent ductus arteriosus (PDA). Corresponding configurations for the closure of such a PDA are also to be seen in FIGS. 75 and 76 which will be discussed in greater detail hereinafter. All those embodiments are approximately of a hat-shaped configuration.

FIGS. 2A through 13 show examples of these variants in respect of weaving or interlacing of wire-like elements, in which respect they show only by way of example the forms which in principle are possible. It will be appreciated that numerous further variants and combinations of the illustrated forms can also be formed. FIG. 2A shows a single-layer mesh comprising two wire-like elements 5, 6. FIG. 2B shows a double-layer mesh comprising wire-like elements 5, 6 in the one layer and wire-like elements 55, 66 in the other layer. FIG. 3C shows a three-layer mesh comprising wire-like elements 5, 6 in the one layer, wire-like elements 55, 56 in the second layer and wire-like elements 555, 666 in the third layer. FIG. 2D shows a single-layer mesh formed by two respective wire-like elements 5, 6 extending in mutually parallel juxtaposed relationship. FIGS. 3 and 4 show variants in which the two wire-like elements 5, 6 extending in mutually parallel relationship with each other are twisted together and the respective twisted pairs of wire-like elements 5, 6 are in turn interlaced with each other. The only difference in these two embodiments is the manner of lacing the individual pairs through each other. In the embodiment shown in FIG. 3 the respective twisted pairs are passed together between the twisted other pairs of wire-like elements, while in the embodiment of FIG. 4 the individual wire-like elements 5, 6 are taken past each other at the intersection points.

FIG. 5 shows further possible ways in which individual wire-like elements can be interlaced with each other, in which respect in the first case two wire-like elements 5, 6 are interlaced with each other, in the second case four wire-like elements 5, 6, 7, 8 are interlaced with each other and the in third case six wire-like elements 5, 6, 7, 8, 9, 50, 60 are interlaced with each other.

FIG. 6 shows an interlacing or gauze variant in which individual smooth wire-like elements 7 are woven or interlaced with interlaced pairs of wire-like elements 5, 6. FIG. 7 shows a variant in which only one single smooth wire-like element 7 is woven or interlaced alternately with a correspondingly smooth wire-like element 7 and with a mesh comprising four wire-like elements 5, 6, 8, 9. In FIG. 8 a combination of a weft arrangement comprising six wire-like elements and a pair of wire-like elements 5, 6 is arranged alternately and interlaced with a pair of twisted wire-like elements. FIGS. 9 and 10 show combinations each comprising five or six interlaced wire-like elements 5, 6, 7, 8, 9, 60 which are again woven or interlaced with each other. FIG. 11 shows a weft arrangement comprising a respective twisted pair of wire-like elements 5, 6. FIG. 12 shows a weft arrangement comprising alternately a smooth wire-like element 7 and a twisted pair of wire-like elements 5, 6. FIG. 13 shows a weft arrangement comprising three smooth wire-like elements 5, 6, 7 which are not interlaced with each other and alternately in a corresponding fashion three smooth wire-like elements and only two smooth wire-like elements 5, 6. The individual wire-like elements can be of a round or flat cross-sectional shape or a cross-sectional shape of any other form.

FIG. 14 diagrammatically shows an embodiment of an implantable device 1 which is of a regular concentric form. In principle it is also possible for the implantable device to be provided with an eccentric form if for example it is to be implanted in the body of the patient at a location which is delimited at one side, for example by a wall or an aorta or in some other form. Embodiments of that nature will be discussed in greater detail with reference to FIGS. 61 through 68. In FIG. 14, two detail sections A, B of the implantable device 1 are marked, which are shown in the detail views in FIGS. 15 (detail A) and 16 (detail B). In this respect, FIG. 15 which shows the center of the implantable device clearly illustrates the small central through opening 16 which extends through the distal portion, the intermediate portion and the proximal portion. Here, the carrier structure 17 is formed in the manner of a regular mesh from a wire-like element 5. The detail B, shown in FIG. 16, of the edge of the implantable device 1 illustrates that that outer edge 18 is wrapped with an additional element 19 serving to fix the membrane element 4. The element 19 can therefore be for example in the form of thread, for example of Prolene, a cardiac-surgical suture material, or in the form of a wire element. Furthermore an additional element can be provided as a marker for clearly identifying the implantable device under a monitoring apparatus during an implantation procedure, as is further described hereinafter. That outer edge 18 of the implantable device is the region in which the distally facing part 14 and the part 13 which faces in the proximal direction of the distal portion adjoin each other or blend into each other. That can also be seen in FIG. 1G and FIG. 1H.

Figure 30:
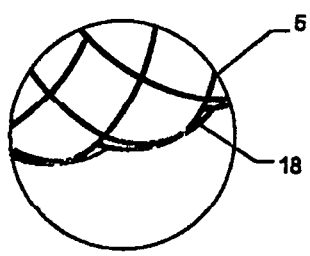
Figure 31:
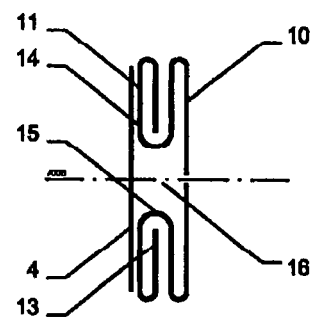
Figure 33:
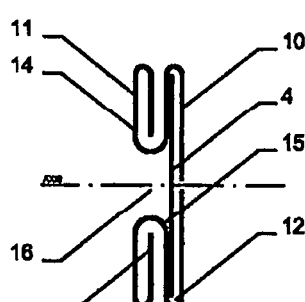
Figure 32:
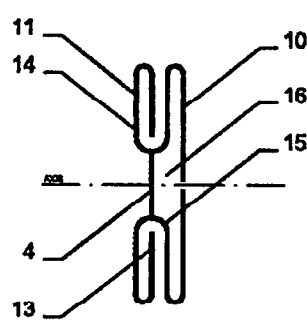
Figure 34:
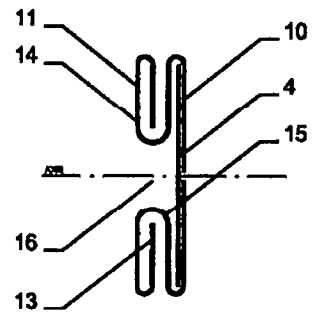
Figure 35:
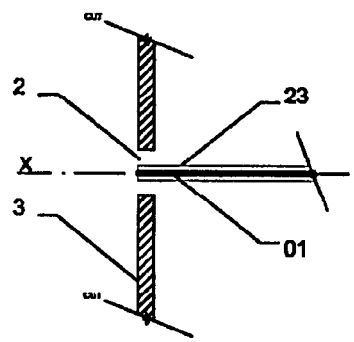
Figure 36:
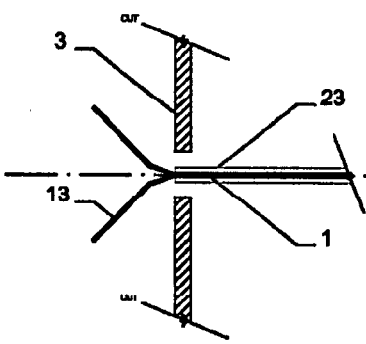
Figure 37:
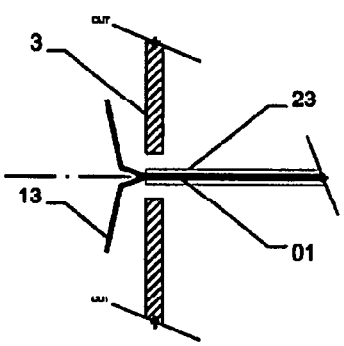
Figure 38:
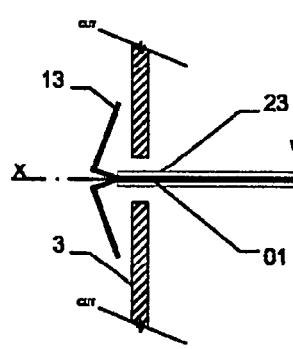
Figure 39:
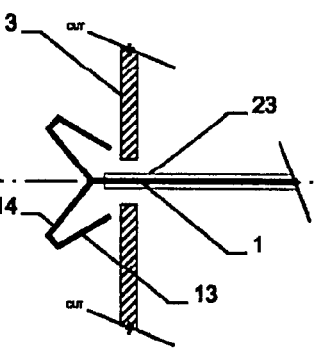
Figure 40:
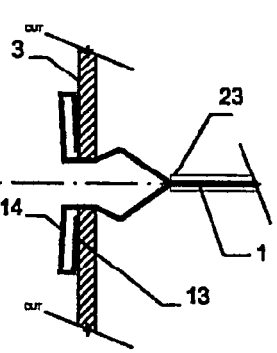
Figure 41:
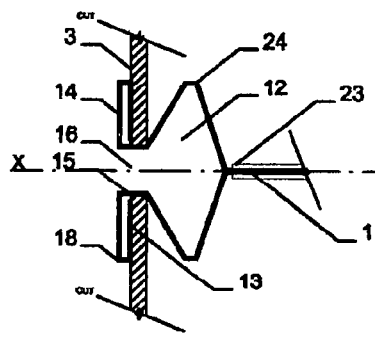
Figure 42:
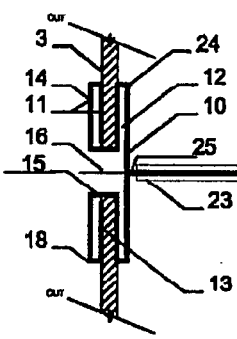
Figure 42:
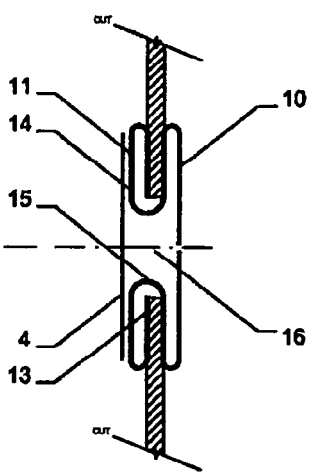
Figure 43:
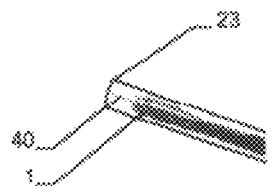
Figure 44:
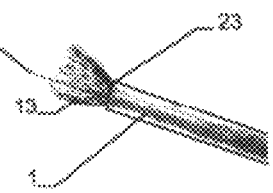
Figure 45:
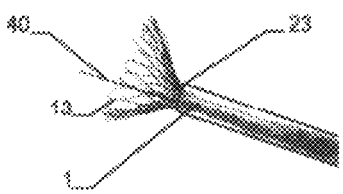
Figure 46:
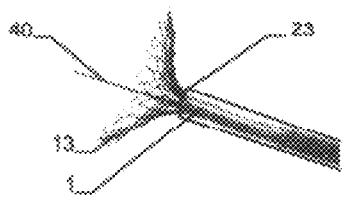
Figure 47:
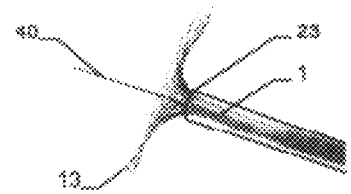
Figure 48:
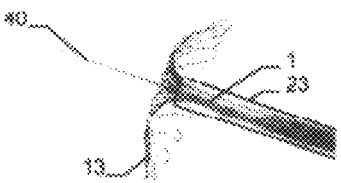
Figure 49:
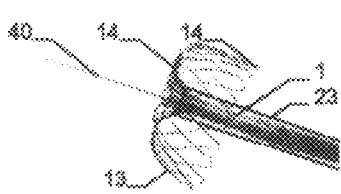
Figure 50:
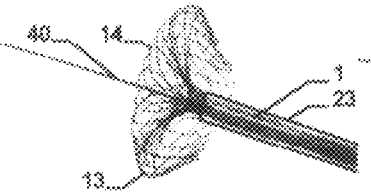
Figure 51:
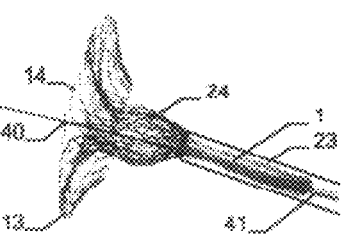
Figure 52:
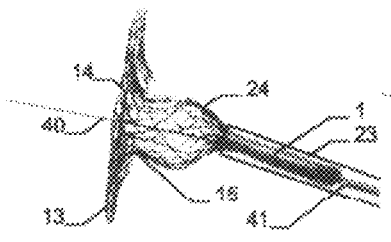
Figure 53:
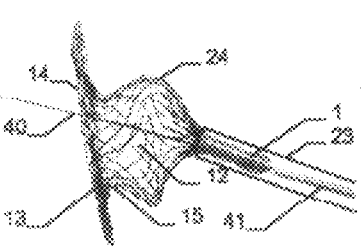
Figure 54:
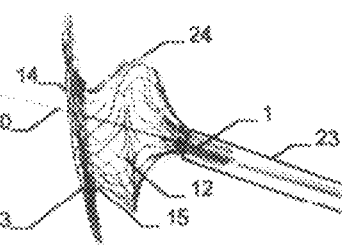
Figure 55:
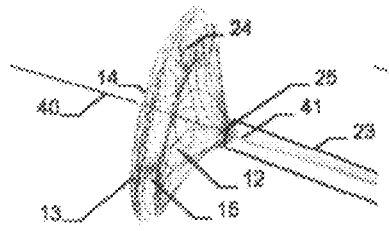
Figure 56:
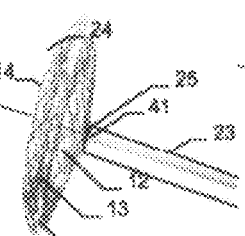
Figure 57:
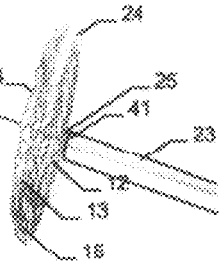

The carrier structure 17 of the implantable device 1 can be so dense and compact that it already forms a kind of membrane. If however that is not the case or if completely sealing closure of an opening such as a defect opening in the heart of a patient is desired, the additional membrane element 4 can be provided, which is diagrammatically shown by way of example in FIG. 16 under the weft or mesh configuration of the carrier structure. As can be seen from FIGS. 30 through 34 the membrane element can be fitted not only distally on the part 14 at that location of the distal portion 11 of the implantable device 1, as FIG. 1 and also FIG. 30 shows, but it can also be provided at other locations within the implantable device and on the outside thereof. The variant shown in FIG. 32 of a very small membrane element 4 is arranged within the opening 16 of the intermediate portion 15. The smaller the membrane element is, the correspondingly less is the clotting risk as only the mesh or gauze of the carrier structure 17, that is to say only the material thereof, is present around the opening 2 which is to be closed in the wall 3, and not a combination of the material of the membrane element and the carrier structure, which otherwise increases the clotting risk and can possibly result in headaches and temporary blindness because of the resulting travelling embolism. Those complications can be reliably avoided here. The same also applies to the other variants in FIGS. 31, 33 and 34, in which respect in FIG. 31 the membrane element is arranged in the internal space of the proximal portion 10 and is fixed for example to the peripherally extending edge 18 on the inside thereof. In FIG. 33 the membrane element is arranged and fixed in the internal space 12 defined by the proximal portion 10, in a condition of bearing against the distal part of the proximal portion 10, which goes into the intermediate portion and which, when the implantable device is disposed in a hole in a wall, bears against that wall. In FIG. 34 the membrane element is provided in the internal space defined by the proximal portion 10, on the proximal inward side thereof. The membrane element can comprise for example a plastic material such as a polymer.

FIG. 17 shows the detail, which is not visible in FIGS. 14 and 16, of the back-folded or rearwardly folded part 13 of the distal portion 11. Here it is of a comparatively narrow configuration. It can equally be wider and can even extend as far as the center of the implantable device.

Figure 21:
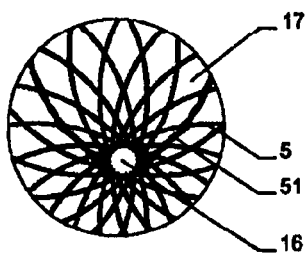

FIGS. 18 and 21 through 23 show an embodiment which is modified in relation to the embodiment of the implantable device 1 in FIG. 14, involving a different configuration for the peripherally extending outer edge 18. In this respect FIG. 18 shows a plan view of the proximal portion 10, FIG. 21 shows a detail view of the center of the implantable device with the small through opening 16 and two ends 51 of the wire-like element 5, which are interlaced centrally in the carrier structure 17 with another portion of the wire-like element 5.

As can be seen from the detail view of the detail D of FIG. 18, in FIG. 22, instead of the outer edge 18 of the proximal portion 10 being wrapped around, this structure only involves loops of the carrier structure being partially wound around with a wire-like element 52 or the like. It serves as a marker for visually indicating the implantable device for example under an X-ray unit. For that purpose for example the wire-like element 52, as illustrated, is in the form of a microspiral produced from a material containing platinum and iridium, for example with a proportion of between 70 and 90% platinum and between 30 and 10% iridium. As can be seen from the detail view of the detail E in FIG. 18, as shown in FIG. 23, that implantable device 1 is also formed from a single wire-like element. Here the end 51 thereof is interlaced in the region of the edge 21 in order to prevent unwanted loosening thereof.

FIG. 19 shows a front view of the proximal portion 10 and FIG. 20 shows a plan view of the distal portion 11 of a further embodiment of the implantable device 1. It will be clear in this respect that, in this embodiment, the proximal portion 10 is provided with a part which is folded rearwardly in a direction towards the distal portion 11 and a part which faces in the proximal direction, that is to say it is of a configurational design corresponding to that of the distal portion shown in FIG. 1. The carrier structure 17 is denser than for example in the embodiment of FIG. 14. That is particularly clearly visible also in the central region as there substantially no through opening is left in the proximal portion 10. The individual, regularly arranged segments of the carrier structure 17 with a repetitive configuration can each occupy for example an angle of a=20°, with a tolerance of 3%.

FIG. 24A shows a diagrammatic side view illustrating the principle of an implantable device in which the distal portion 11 is of a flat or even configuration whereas the proximal portion 10 is of a curved closed configuration. In FIG. 24B the distal portion 11 is formed with parts 13, 14 which are folded back on to each other.

Figure 25:
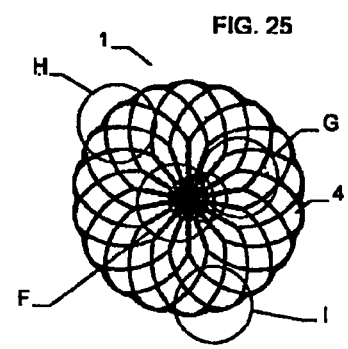
Figure 26:
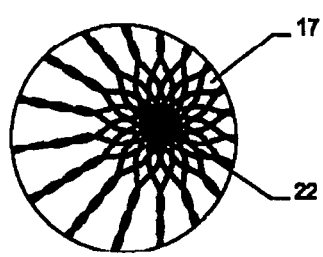
Figure 27:
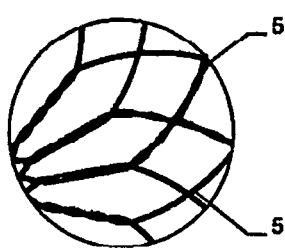
Figure 28:
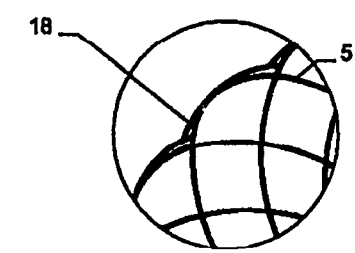
Figure 29:
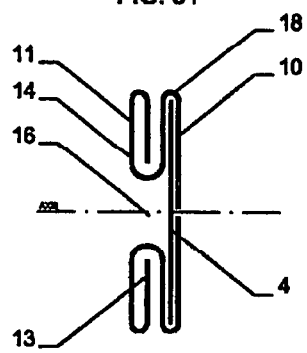

The embodiment of the implantable device shown in FIG. 25, unlike that shown in FIG. 14 and also like that shown in FIGS. 19 and 20, has essentially no through opening as the proximal portion 10 does not have such a central opening, but is of a substantially closed configuration in its central region 22, as can be seen from the detail view of the detail F marked in FIG. 25, in FIG. 26. In order to make the carrier structure stable but more open in the region surrounding the central region, the individual wire-like elements are interwoven in a region surrounding the central region 22 of the carrier structure 17, as can be seen from the detail view of the detail G identified in FIG. 25, in FIG. 27. The end 51 of the wire-like element 5 is interwoven in that central region 22 with a part of the wire-like element in order to secure it to prevent unwanted loosening thereof. Here the outer edge 18 is not wrapped around with an element fixing the membrane element as no membrane element is provided. That can be seen both from the detail view of the detail H of the edge 18 in FIG. 28 and also the detail view of the detail I of FIG. 25, as shown in FIG. 29.

FIG. 59 shows the embodiment of the implantable device of FIG. 25 in modified form with a membrane element 4 fixed thereto. The membrane element 4 bears against the entire carrier structure 17 so that no peripherally extending edge of the carrier structure remains free. The risk of embolism occurrence in the edge region of the implantable device 1 is thus low. The membrane element 4 also extends over the inner region 29, shown in FIG. 59, of the proximal portion and over the proximal end 25 which here is of a substantially closed nature. The membrane element 4 is fixed to the peripherally extending edge 24 of the carrier structure 17 of the implantable device 1, for example being sewn thereto.

FIGS. 35 through 42B diagrammatically show the procedure involved in placement of an implantable device 1 in the opening 2 in the wall 3. FIGS. 43 through 58 show that by way of the example of a high-detail implantable device 1 which is shown in a perspective view. In the first step in FIG. 35 and FIG. 43, a guide or ejection wire 40 and subsequently a catheter 23 which encloses it and in which the implantable device is disposed within the catheter 23 in a primary condition of being elongated along the axis x, surrounding the ejection wire, is pushed through the opening 2. To produce the advance movement for example a holding wire 41 which is fixed to the implantable device 1 is moved relative to the ejection wire 40. The manner of fitting the holding wire 41 to the implantable device will be described in greater detail hereinafter with reference to FIGS. 78 through 89. In the second step the implantable device 1 is pushed out of the catheter 23 along the ejection wire 40. In that case, the part 13 of the distal portion 11 which will later bear against the wall 3 is firstly deployed. That can be seen in particular from FIGS. 36 and 37 and FIGS. 44 through 47. It can be clearly seen in that respect that a configuration is imparted to the part 32, to cause it to fold back in the proximal direction. Advantageously the material for the implantable device 1 is a shape memory material, in particular Nitinol, a plastic material or another shape memory material or a combination of a shape memory material and another material, for example in the case of a multi-layer carrier structure of the implantable device.

When the implantable device 1 is further pushed out of the catheter 23 the second part 14 of the distal portion 11 is deployed, as can be seen from FIGS. 39 and 48 through 50. The further the implantable device is pushed out of the catheter, the correspondingly further is the part 13 folded back on to the part 14 and bears against same when the implantable device 1 is further pushed out of the catheter 23.

When the implantable device 1 is further pushed out of the catheter, the proximal portion 10 is also progressively deployed, as can be seen from FIGS. 40 through 42 and 51 through 57. In that case the proximal portion 10 expands radially and forms a peripherally extending edge 24 so that the proximal portion is also of a double-layer configuration. It will be noted however that the proximal end 25 of the proximal portion 10 is held together closed or is of such a configuration as to be provided with a minimum opening so that the internal space 12 is delimited thereby.

When the implantable device has been pushed completely out of the catheter and in that case has been deployed into its secondary form, it is for example of the shape shown in FIGS. 42A or 42B and 58. Unlike the embodiment shown in FIG. 42A the embodiment of FIG. 42B is provided with a membrane element 4 on its distal portion. Instead of a substantially flat shape in respect of the proximal portion 10, as is shown in these Figures, it can also be of a bulging configuration, that is to say it can enclose a larger internal space, and/or can be curved, as is shown for example in FIG. 24B.

When the implantable device is fitted at the implantation location in such a way that the desired closure or partial closure is afforded, the implantable device can be separated from the ejection system in the form of the ejection wire 40 and holding wire 41. A corresponding view is to be found in FIGS. 42B and 58. If further adjustment is still required, that can be effected by further relative movement of the ejection wire and the holding wire until the desired position is reached. In that respect, rotation of the implantable device is also possible, as for example FIG. 87 shows, being a diagrammatic plan view on an implantable device with ejection and holding wires passing therethrough. Flotation of the implantable device around the ejection wire 40 and the holding wire 41 is also possible, as diagrammatically shown in FIG. 88. The guide or ejection wire 40 is overall of a very thin nature and has a very thin tip, whereby flotation of an implantable device is possible with the ejection wire. The tip of the ejection wire can be of a diameter of between 0.1 and 0.3 mm. The implantable device can assume any angle in relation to the ejection wire 40, as indicated in FIG. 86. In that way it is possible for the implantable device to be directed without any problem even at implantation locations which otherwise involve difficult access, in a human or animal body.

As can be seen from the plan view of the implantable device 1 in FIG. 60, this embodiment in comparison with that shown in FIG. 58 involves the modification that it is provided with a membrane element 4. It is of a smaller diameter than the implantable device 1 so that an edge of the carrier structure 17 remains free in peripherally extending relationship around the membrane element 4. The membrane element 4 is fixed on the distally directed part 14 of the distal portion 11, in particular being glued or sewn thereto. The ejection wire 40 is passed through the center of the implantable device 1 and the membrane element 4, as FIG. 60 also indicates.

The positioning of the implantable device can be tracked for example by way of imaging processes, in which case for example the implantable device at some locations can have the above-mentioned markers 52 which are visible when the imaging processes are used. Those markers can be provided for example at the edge, as shown in FIG. 22, or in the surface of the carrier structure 17, in which respect arranging them at the edge is found to be more advantageous as the boundary contour of the implantable device can be clearly detected.

The implantable device 1 can adapt to any shape of an opening 2 within which it is arranged. For example it becomes oval when it is fitted in an oval opening or polygonal when it is fitted in a polygonal opening. FIGS. 61 through 64 show embodiments of such deformations. In this case the entire implantable device can curve around all axes in order to adapt to the configuration at the implantation location, in particular to walls there. By virtue of the portion which is of a double-layer configuration by virtue of the rearwardly folded part of the one portion, the implantable device adapts without any problem to all configurations at the implantation location and assumes a stable position in spite of deformation and is even clamped fast at the implantation location.

In order still further to improve implantation, the implantable device can also already be provided with a curvature and/or an oval, polygonal or other configuration, when its secondary form is imparted thereto, upon production thereof, in order better to fit into a correspondingly shaped opening. An embodiment of that kind is shown by way of example in FIG. 65. Here, the distal and the proximal portions 10, 11 are partially bent away from each other like the open mouth of an animal. For better orientation, FIG. 65 shows not only the two parts 13, 14, which are folded on to each other, of the portion 11 and the portion 10, but also the intermediate portion 15 and the outer edge 18 of the portion 11. That particular configuration which is imparted to the implantable device 1 is provided for example in order to avoid an adverse pressure on an aorta. As can be seen from FIGS. 66 through 68 the implantable device can be placed around such an aorta 31 so that the risk of damaging the aorta wall no longer arises. In that respect FIG. 66 shows a plan view of the implantable device 1 which is provided with a membrane element 4 while FIGS. 67 and 68 show side views of the implantable device 1. In all cases the implantable device can be clearly seen to be fitted around the aorta 31. As can be seen from FIG. 68 the intermediate portion can also be arranged eccentrically with respect to the implantable device so that, in plan view, the result is that the implantable device is of an eccentric configuration.

The implantable device can be used in relation to the most widely varying range of problems, for example as an ASD, VSD or PFO closure device, a PDA closure device, a vascular closure device or a left cardiac auricle closure device.

FIGS. 69 through 74 show further embodiments of the implantable device 1 in which however, in contrast to the preceding embodiments, at least one portion is wound up in a helix-like configuration. In this case, in addition to the two parts 13 and 14 in which the part 13 is folded back or rearwardly on to the part 14, at least one further rearward or back folding is effected by the implantable device when it is further pushed out of a catheter and when the secondary form thereof is produced. The two parts 13 and 14 are also folded at least once around themselves. That provides that this portion is even more stable in comparison with the implantable devices in the state of the art.

The part which is firstly deployed upon deployment of the implantable device 1 from a primary form into a secondary form is the part 133. When the implantable device is further pushed out of a catheter 23, the part 133 is followed by the part 144 which is folded in the distal direction whereas the part 133 is folded in the proximal direction. When the implantable device is further pushed out of the catheter the part 13 is folded on to the part 133 and subsequently the part 14 is folded on to the part 144. Although not shown in the Figures, still further parts can be folded on to each other in that fashion so that the result afforded is a helix of greater or lesser thickness.

Figure 69:
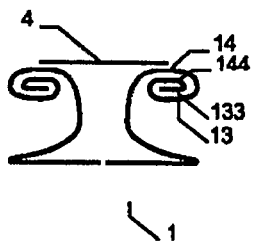
Figure 70:
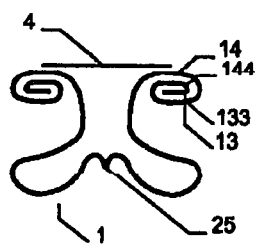
Figure 71:
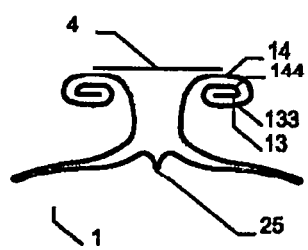

The rest of the configuration of the implantable device 1 can be as desired, as in the other embodiments. As shown in FIG. 69 only the one portion is provided with a helix-like configuration whereas the other is of a substantially flat disk-shaped or anvil-like configuration and has a small through opening. The through opening 16 is closed in the helix-like portion by a membrane element 4 which is arranged at the outside. In the case of the embodiment of FIG. 70 once again the once portion is of a helix-like configuration. The other portion is shaped in a bulging curved configuration, with an inwardly retracted proximal end 25 which is held together. Unlike the embodiment of FIG. 70, the embodiment of FIG. 71 provides that the proximal portion is shaped in a substantially flatly curved configuration and is of a larger diameter than the helix-like portion. The inner end 25 of the proximal portion is also brought together. In contrast thereto, the proximal portion shown in FIG. 74 is of approximately the same diameter as the helix-like portion and has a membrane element 4 within the closed curved portion.

Figure 72:
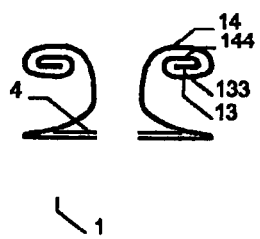

The embodiment of FIG. 72 is similar to that shown in FIG. 69 but with the difference that a comparatively large through opening is provided in the disk-shaped portion and a membrane element 4 is arranged there. The through opening in the disk-shaped portion approximately corresponds to the through opening through the implantable device itself.

The embodiment shown in FIG. 73 has two portions which are wound or folded up in a helix-like configuration. In this case the proximal portion 10 also has a part 110 which is folded back or rearwardly in the proximal direction and which goes into a distally facing part which in turn goes into a proximally facing part. The proximal portion can therefore also be of a helix-like configuration by parts being folded over on to each other a plurality of times.

FIGS. 75 and 76, like above-mentioned FIG. 1K, also show a hat-shaped configuration of the implantable device 1, which is suitable for use for closing a PDA. In this case the implantable device is inserted into the defect opening and the one portion bears against the aorta wall. Preferably that is the portion which is provided with the part that is folded back at least once, as that portion can assume a corresponding configuration or can even adopt it as having been imparted thereto as the secondary form thereof. The hat shapes in the above-mentioned Figures are therefore particularly suitable as the respective hat brim, as the portion 26 which is folded back or rearwardly at least once, can adapt to the configuration of the aorta wall and can be stably held fast there. The embodiment of FIG. 1K has only one short rounded portion 27 which forms the head part of the hat whereas in FIG. 76 there is a particularly long, approximately cylindrical head part portion. The latter has a closed end which in addition is of such a shape as to be drawn inwardly towards the other portion forming the hat brim. The portion forming the hat brim can be shaped in a curved configuration transversely with respect to the longitudinal extent of the implantable device in order to be able better to adapt to an aorta wall or another wall at the implantation location.

FIG. 75 shows a configuration of the implantable device 1, which protrudes at both portions. The hat shape not only has the protruding hat brim portion 26 but also a head part portion 27 which protrudes at the end. Both portions can be of a configuration or curvature which is adapted to the configuration at the implantation location and can have parts which are folded back or rearwardly, like the parts 13, 14.

Besides the hat-shaped embodiments of the implantable device, which are shown in the Figures, it is also possible to provide inclined shapes, shapes which are made up in a pear configuration for the head part portion, shapes which are turned over inwardly one or more times etc for adaptation to a respective implantation location.

FIG. 77 shows an embodiment of the implantable device 1 on an ejection wire 40 arranged in a sheathing 42 for stabilisation purposes. The implantable device 1 has a bulging closed portion 10 and a disk-shaped portion 11 with parts which are folded back on to each other. The procedure involved in threading the at least one holding wire 41 on the implantable device 1 is shown in detail in FIGS. 78 through 81. Similarly to the situation with the embodiment of the implantable device 1 shown in FIG. 25 and FIG. 26 respectively, loops 87 as ends of twisted portions 88 of the wire-like elements 5, are formed around a through opening through in particular the proximal portion 10 of a proximal end 25 which is held together or which can be held together. The holding wire 41 is threaded through those loops 87, as shown in FIGS. 78 through 81. Such a loop 87 with twisted portion 88 adjoining same can be seen in the detail view in FIG. 82 and the diagrammatic plan views of a number of eight loops 87 arranged in a circular configuration, with twisted portions 88, in FIGS. 83 through 85.

The holding wire is doubled within and outside the loops 87. At the end of the holding wire 41 it therefore forms an eye loop 81. As already mentioned, the ejection wire 40 has a very thin tip so that it can be particularly easily threaded through the end eye loop 81 of the holding wire 41. In addition the ejection wire is mostly also threaded through the center, that is to say the through opening in the proximal portion and naturally as much as possible also of the distal portion and a membrane element 4 if such is provided.

The end 81 of the holding wire 41, which is shown in FIG. 82, is held together with the end of the ejection wire for manipulation of the ejection procedure at a proximal location, by the operator. The end 82 of the holding wire 41 is therefore not provided so close to the implantable device as can be assumed from FIG. 81 as the at least one holding wire 41 is of a length which as much as possible goes beyond the length of the catheter 23 used for the implantation operation.

Figure 83:
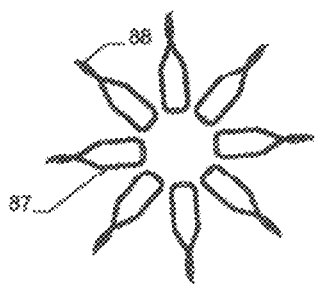

As can be seen from FIG. 84 the loops can not only be arranged in a condition of not being connected in mutually juxtaposed relationship, surrounding the inner through opening, as can be seen from FIG. 83, but they can also be connected to a carrier ring 85. The ejection wire 40 which is threaded through the eye loop 81 of the holding wire 41 then goes for example as shown in FIG. 85 through the carrier ring, in which case the holding wire does not need to be threaded through all loops 87 but threading through a loop 87 and/or looping around the carrier ring 85 is also sufficient to fix the holding wire 41 in the implantable device.

FIG. 89 shows a detail view of an implantable device 1 through which the ejection wire 40 and the holding wire 41 pass, wherein the holding wire 41 and the ejection wire 40 are arranged in the sheathing 42 within the catheter 23 in order to achieve better stability upon being pushed through the catheter.

Figure 90:
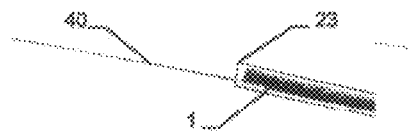

FIGS. 90 through 101 show the deployment of another embodiment of the implantable device 1 from an elongated primary form which it assumes in the catheter 23 into a secondary form which it assumes outside same as soon as it has been deployed and which was imparted thereto previously upon manufacture thereof. In that respect FIG. 90 shows the elongated primary form of the implantable device, where it is still arranged within the catheter 23, with the ejection wire 40 extending through the catheter 23 and the implantable device 1. The ejection wire 40 is suitably fixed to the implantable device 1, for example as shown in FIGS. 78 through 85.

Figure 91:
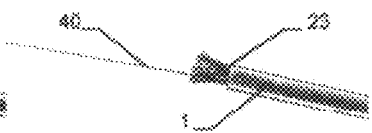
Figure 92:
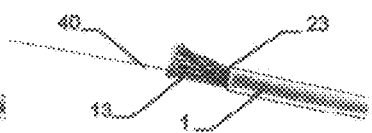
Figure 93:
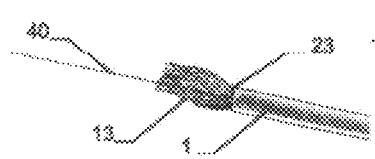
Figure 94:
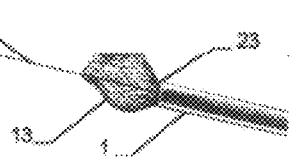
Figure 95:
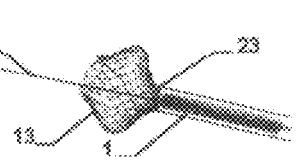
Figure 96:
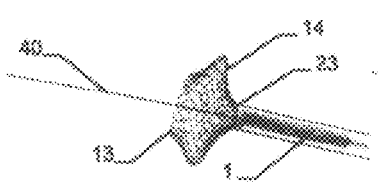
Figure 97:
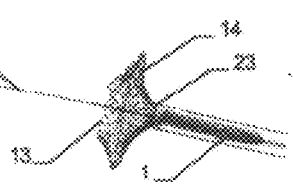
Figure 98:
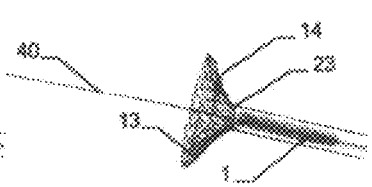

FIGS. 91 and 92 show the implantable device in a position of already having been pushed a distance out of the catheter 23, wherein the part 13 of the implantable device is the first pushed out of the catheter. In the view shown in FIG. 93 the part 13 is already beginning to fold in. Now, that folding-in movement is not outwardly, as in the above-described embodiments, but inwardly in a direction towards the ejection wire 40. That can be particularly clearly seen from FIGS. 94 through 97.

The part 14 of the implantable device 1, which in this embodiment faces towards the other portion 10 which is still disposed in the catheter 23, also further deploys when the implantable device is further pushed out of the catheter. As can be seen from FIG. 98 a funnel configuration is formed, the distal end of which is of a double-layer nature by virtue of the (inner) part 13 which folds back inwardly on to the outer part 14, and it is therefore distally of greater stability.

Figure 99:
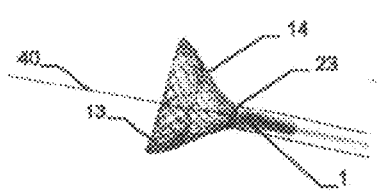
Figure 100:
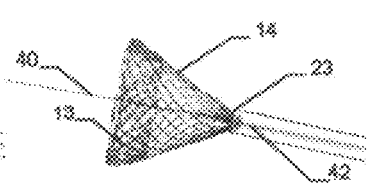
Figure 101:
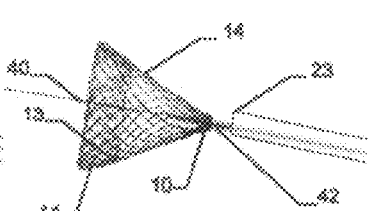

When the implantable device is further pushed out of the catheter the funnel configuration of the overall implantable device becomes even more clear (see FIGS. 99 through 101). In that case the outer part 14 of the distal portion 11 goes into the proximal portion 10. The latter has a proximal end which is held together and which is substantially closed. That end is engaged by the sheathing 42 of the ejection wire 40 for stabilisation thereof so that the implantable device 1 can be pushed out of the catheter 23 without any problem.

It will be seen that, when the part 13 is folded inwardly in a direction towards the ejection wire, stabilisation of that portion 11 of the implantable device 1 can admittedly also be implemented. That kind of inward folding movement for stabilisation purposes is suitable in relation to numerous uses and forms of the implantable device, such as for example the funnel configuration show in FIG. 101. It will be noted however that, when the part 13 is folded inwardly in the direction towards the ejection wire 40, the problem arises that folding into the primary form of a secondary form which in particular has been completely deployed is scarcely possible. Retraction of the deployed implantable device into the catheter is found to be difficult by virtue of the double-layer material as the latter will scarcely pass through the catheter 23 and therefore a different catheter of a larger inside diameter would have to be used. That however is quite complicated and expensive. Therefore, for the situation involving the implantable device being pulled into the catheter 23 after deployment of the part 13 on to the part 14, retraction of the part in an outward direction, as is the case in the above-described embodiments, is more advantageously appropriate as in that case the device can be folded back from the secondary form into the primary form without any problem.

The above-described implantable devices can be coated or treated on their surfaces. That surface treatment or coating can be provided on the material used for forming the carrier structure and/or on the carrier structure when it is in the finished shaped condition. An overview of materials which can be used in that respect and processes for treatment of the surfaces is set forth hereinafter.

Suitable inorganic and ceramic materials are in particular biogold, gold, DLC (diamond-like carbon), DLN (diamond-like nanocomposite), iridium oxide which is particularly suitable for surface passivation and anti-oxidative coatings, nanoporous $Al_2O_3$ (drug eluting), silicon carbide, HaP (hydroxylapatite) and titanium nitrite oxide.

Suitable synthetic polymers are in particular parylene C (poly(2-chloro-p-xylylene)), PBMA (polybutylmethacrylate), PC (phosphorylcholine), PE (polyethylene), PEVA (polyethylene vinylacetate), PHMA (polyhexylmethacrylate), Polyzene$^a$-F (PTFEP or poly[bis](trifluoroethoxy) phosphazene), PTFE (polytetrafluoroethylene) and PU (polyurethane), wherein that is particularly also suitable as a thin layer. Further synthetic polymers with a corresponding positive action in relation to the implantation location (assisting with an embolism procedure, preventing clot formation etc) can also be used.

In particular collagen, chondroitin sulfate, elastin, fibrin and hyaluronic acid are suitable in the area of human biopolymers which can also advantageously be used.

Furthermore the surfaces can also be provided with pure medication coatings such as for example with abciximab (as a glycoprotein inhibitor), heparin (as a blood coagulation inhibitor) and/or paclitaxel (conventionally used for interfering with cell division). It is also possible to provide other pure medication coatings.

In addition it is possible to use medication-liberating polymers such as for example cellulose for liberating abciximab, PC for liberating angiopeptin, PE for liberating DNA, PEVA/PBMA for liberating rapamycin, poly(L-lactide) (PLLA) for liberating a medication which can be selected in use-specific fashion, polylactide (PLA) for liberating paclitaxel or hirudin or iloprost, PLA-PC for liberating a viral vector, and PU for liberating forskolin. Other combinations of polymers and medications can also be effective. In that respect a viral vector can be used for introducing genetic material into cells of living organisms. The above-mentioned polymers are mostly resorbable biomaterials so that the specified medications can correspondingly deploy their action whereas the polymers do not have any adverse action on the organism of the patient. By way of example rapamycin mostly has a strongly cytotoxic action and is used to prevent rejection reactions from occurring. Hirudin has a blood coagulation-inhibiting action and iloprost has a vessel-dilation and vessel-protection effect.

It is also possible to provide functionalised surfaces with biomolecules and functional groups as a surface coating for the implantable device, for example in the context of what is referred to as molecular surface engineering. In that case functionalised surfaces are afforded from unmodified surfaces by the introduction of functional groups. Inter alia in that case it is possible to produce boundary surfaces which involve specific functions.

In the field of gene technology it has been found that stem cells can also be advantageously used for the surface coating of implantable devices. By way of example the surface of stents or other implantable devices can be specifically provided with cell ligand structures for the adhesion of progenitor cells circulating in the blood.

Suitable processes for the surface treatment are in particular processes for depositing, removing or altering boundary layers such as for example plasma treatment which is used in particular in relation to DLC and DLN (diamond-like carbon, diamond-like composite), the PVD process (physical vapor deposition) or the CVD process (chemical vapor deposition), ion implantation, sputtering, the ion beam process, the laser process, a thermal process, spin coating, dip coating, etching or electropolishing. It is also possible to use other surface treatment processes. The term spin coating is used to denote the application of a uniformly thin film to a flat rotationally symmetrical substrate by the distribution of a material under centrifugal force with rapid rotation of the substrate. The term dip coating is used to denote coating a substrate involving translational symmetry by dipping same into a material (sol), pulling it out at a constant speed so that a liquid film remains clinging to the substrate surface, and drying thereof.

Besides the embodiments of implantable devices which have been described hereinbefore and which are shown in the Figures it is also possible to form many other configurations in which at least one of the distal and proximal portions in the secondary form has an outwardly facing part and a second part which is the first to be deployed from the primary form into the secondary form and which is folded back or rearwardly on to the first part. In that respect the two parts in the completely deployed form of the implantable device can lie one upon the other or can be disposed at a spacing relative to each other, wherein the part facing towards the other portion can be supported against the wall of a defect opening or the implantation location.

In any of the cases, by virtue of the at least double-layer configuration, that portion of the implantable device is stabilised. Instead of the described and illustrated flat configuration of the proximal outward side of the proximal portion, it can also have an end which is brought together for example centrally in such a way that it projects outwardly. The described features can be provided individually or in any combination with each other and in that respect form advantageous configurations of the invention. All features which have been set forth in relation to the various embodiments of implantable devices, in particular those which concern the carrier structure and/or a membrane element, can be provided in all those embodiments, even if they are possibly described only in relation to one or other thereof. Accordingly any combination of the individual embodiments and the features thereof is possible.

LIST OF REFERENCES 1 implantable device
2 opening
3 wall
4 membrane element
5 wire-like element
6 wire-like element
7 wire-like element
8 wire-like element
9 wire-like element
10 proximal portion
11 distal portion
12 internal space
13 part
14 part
15 intermediate portion
16 opening/central through opening
17 carrier structure
18 outer edge
19 element
20 inner region
21 outer edge
22 central region
23 catheter
24 peripherally extending edge
25 proximal end
26 hat brim portion
27 head part portion
30 outward side of the wall
31 aorta
40 ejection wire
41 holding wire
42 sheathing
50 wire-like element
51 end
52 wire-like element
55 wire-like element
60 wire-like element
66 wire-like element
81 eye loop
82 end
85 carrier ring
87 loop
88 twisted portion
110 part
133 part 144 part
555 wire-like element
666 wire-like element
x axis

What is claimed is:

1. An implantable device for use in a human and/or animal body for closure or partial closure of defect openings, cavities or organ passages, or for providing a defined communicating opening between walls, organs or cavities comprising:
   a carrier structure which in a primary form has a large ratio of length to transverse extent along an axis and in a secondary form has a smaller ratio of length to transverse extent along the axis, wherein the carrier structure is in the form of a weft, mesh, layered cloth, gauze, or combination thereof, wherein:
   in the primary form said carrier structure comprises a distal portion comprising first and second segments, a proximal portion, and an intermediate portion between the distal and proximal portions, the second segment being at the distal end of the carrier structure adjacent the first segment, each portion and segment having an interior surface and an exterior surface, the distal and intermediate portions capable to deploy from the primary form into the secondary form; and
   in the secondary form, the first segment and the second segment define a substantially u-shaped structure as viewed in a longitudinal cross-section, in which the exterior surface of the first segment faces the exterior surface of the second segment, and the interior surface of the second segment faces the exterior surface of the intermediate portion in a direction towards the proximal portion, the first segment and intermediate portion forming a substantially n-shape structure, as viewed in a longitudinal cross-section, encompassing the second segment.

2. The implantable device as set forth in claim 1, wherein the intermediate portion has a diameter which is reduced in relation to the proximal and the distal portions.

3. The implantable device as set forth in claim 2, wherein the diameter of the intermediate portion, the diameter of a through opening extending through the implantable device, or a combination thereof is predeterminably dimensioned for providing a defined communicating opening between the walls, organs or cavities in the human and/or animal body.

4. The implantable device as set forth in claim 2, wherein the second part segment of the distal portion extends between said two legs such that it is close to the intermediate portion or bears against the intermediate portion.

5. The implantable device as set forth in claim 1, wherein at least the distal portion is of a substantially disk-shaped or bulging configuration in the secondary configuration.

6. The implantable device as set forth in claim 5, wherein the carrier structure has a substantially closed end.

7. The implantable device as set forth in claim 6, wherein the substantially closed end brings together ends of the carrier structure defined by said weft, mesh, layered cloth, gauze, or combination thereof.

8. The implantable device as set forth as set forth in claim 1, wherein the distal portion is substantially disk-shaped and the proximal portion is of a bulging configuration in the secondary configuration.

9. The implantable device as set forth in claim 1, wherein the implantable device is shaped to be adapted to a configuration at an implantation location as the secondary form.

10. The implantable device as set forth in claim 1, wherein the second part of the distal portion comprises a peripherally extending thin edge.

11. The implantable device as set forth in claim 1, wherein the carrier structure comprises a shape memory material or a plastic material.

12. The implantable device as set forth in claim 1, wherein the distal portion of the carrier structure is deployable independently of the proximal portion.

13. The implantable device as set forth in claim 1, wherein the carrier structure is formed from at least one wire-like element.

14. The implantable device as set forth in claim 13, wherein the at least one wire-like element is a round cross-sectional shape, a flat cross sectional shape, or a combination thereof.

15. The implantable device as set forth in claim 13, wherein the at least one wire like element comprises a plurality of wire like elements each having an end, wherein the ends of the wire like elements are woven together in a surface of the carrier structure.

16. The implantable device as set forth in claim 1, wherein the carrier structure forms one or more loops at an end of the carrier structure.

17. The implantable device as set forth in claim 16, wherein the one or more loops go into a twisted or interwoven portion.

18. The implantable device as set forth in claim 1, wherein at least one of the proximal and distal portions of the carrier structure is wound up in a helix-like configuration.

19. The implantable device as set forth in claim 18, wherein the distal portion is wound up in a helix-like configuration.

20. The implantable device as set forth in claim 18, wherein the at least one of the proximal and distal portions which is wound up in a helix-like configuration has a plurality of parts facing towards the other of the proximal and distal portions and a plurality of parts facing away from the other of the proximal and distal portions.

21. The implantable device as set forth in claim 18, wherein one of the proximal and distal portions of the carrier structure is wound up in a helix-like configuration and the other of the proximal and distal portions is of a different configuration from the portion which is wound up in a helix-like configuration.

22. The implantable device as set forth in claim 21, wherein the other of the proximal and distal portions is of a substantially flat configuration, a partially bulging configuration, a curved configuration, or a combination thereof.

23. The implantable device as set forth in claim 18, at least one of the proximal and distal portions comprises a through opening.

24. The implantable device as set forth in claim 18, at least one of the proximal and distal portions is substantially closed.

25. The implantable device as set forth in claim 1, wherein the carrier structure is of a hat-shaped configuration with at least one double-layer hat brim-shaped portion.

26. The implantable device as set forth in claim 25, wherein the double-layer hat brim-shaped portion is provided by the distal portion.

27. The implantable device as set forth in claim 25, wherein a head part-shaped portion of the carrier structure is arranged in opposite relationship to the hat brim-shaped portion, and is turned over inwardly into an interior of the implantable device.

28. The implantable device as set forth in claim 1 additionally including an ejection system for said implantable device and ejecting the implantation device in an implantation procedure, comprising at least one guide or ejection wire and at least one holding wire, wherein the at least one ejection wire is provided with a tip.

29. The implantable device having said ejection system as set forth in claim 28, wherein the tip is of a diameter of between about 0.1 and 0.3 mm.

30. The implantable device having said ejection system as set forth in claim 28, wherein the holding wire forms at least one loop for passing the ejection wire therethrough.

31. The implantable device having said ejection system as set forth in claim 30, wherein the holding wire is threadable through one or more end loops of the carrier structure for fixing to the implantable device.

32. The implantable device having said ejection system as set forth in claim 30, wherein the holding wire is threadable through a carrier ring interconnecting a plurality of end loops of the implantable device.

33. The implantable device having said ejection system as set forth in claim 28, wherein the implantable device is rotatable and floatable about the at least one ejection wire and the at least one holding wire.

34. An implantable device for use in the human and/or animal body for the closure or partial closure of defect openings, cavities or organ passages comprising:
a carrier structure which can be reproducibly converted from a primary form into a secondary form which is imparted thereto, wherein the carrier structure has a proximal portion, a distal portion, and an intermediate portion connecting the proximal and distal portions, each portion and segment having an interior surface and an exterior surface, the carrier structure being in the form of a weft, a mesh, a layered cloth, a gauze, or a combination thereof and wherein:
the distal portion comprises a first segment and a second segment;
the first segment and the second segment define a substantially u-shaped structure as viewed in a longitudinal cross-section, in which the exterior surface of the first segment faces the exterior surface of the second segments, and the interior surface of the second segment faces the exterior surface of the intermediate portion in a direction towards the proximal portion, the first segment and intermediate portion forming a substantially n-shape structure, as viewed in a longitudinal cross-section, encompassing the second segment; and
the distal portion is of an outwardly opening form and the proximal portion is of a bulging closed form.

35. The implantable device as set forth in claim 34, wherein at least one membrane element is provided in a region of the proximal portion, the distal portion the intermediate portion, or a combination thereof.

36. The implantable device as set forth in claim 35, wherein the membrane element is fixed to the carrier structure.

37. The implantable device as set forth in claim 35, wherein the membrane element is sewn to the carrier structure.

38. The implantable device as set forth in claim 35, wherein:
the carrier structure comprises edge loops; and
said implantable device further comprises a thread-like element looped around an edge of the membrane element and said edge loops, the thread-like element being knotted at one or more of said edge loops to fix the membrane element to the carrier structure.

39. The implantable device as set forth in claim 35, wherein dimensions of the membrane element approximately correspond to those of a defect opening to be closed.

40. The implantable device as set forth in claim 35, wherein the membrane element is configured and fixed to the implantable device such that the membrane element substantially completely covers over the distal portion when said implantable device is in the secondary form.

41. The implantable device as set forth in claim 35, wherein the membrane element comprises a plastic material.

42. The implantable device as set forth in claim 35, wherein at least one surface of the carrier structure, the membrane element, or a combination thereof is coated or treated with at least one functional material.

43. The implantable device as set forth in claim 42, wherein the functional material is selected from the group consisting of inorganic materials, ceramic materials, synthetic polymers, human biopolymers, medication coatings, medication-liberating polymers, biomolecules, functional groups and genetic materials.

44. The implantable device as set forth in claim 43, wherein the functional material is selected from the group consisting of gold, biogold, diamond-like carbon (DLC), diamond-like nanocomposite (DLN), iridium oxide, nanoporous Al2O3, silicon carbide, hydroxylapatite, titanium nitrite oxide, poly (2-chloro-p-xylylene), polybutylmethacrylate, phosphorylcholine, polyethylene, polyethylene vinylacetate, polyhexymethacrylate, poly[bis](trifluoroethoxy)phosphazene, polytetrafluoroethylene, polyurethane, collagen, chondroitin sulfate, elastin, fibrin, hydraluronic acid, abciximab, heparin, paclitaxel, abciximab-liberating cellulose, angiopeptin-liberating phosphorylcholine, DNA-liberating polyethylene vinylacetate or polybutylmethacrylate, a medication-liberating or substance-liberating poly(L-lactide), paclitaxel or hirudin or iloprost-liberating polylactide, viral vector-liberating polylactide-phosphorylcholine, forskolin-liberating polyurethane and stem cells.

45. The implantable device as set forth in claim 42, wherein the at least one surface of the carrier structure is treated by plasma treatment, a PVD process, a CVD process, ion implantation, sputtering, an ion beam process, a laser process, a thermal process, spin coating, dip coating, etching or electropolishing.

46. The implantable device as set forth in claim 34, wherein the carrier structure acts as a membrane element.

47. The implantable device as set forth in claim 34, wherein the implantable device is of a concentric or eccentric form.

48. The implantable device as set forth in claim 34, wherein the carrier structure automatically adapts to a configuration at an implantation location.

49. The implantable device as set forth in claim 48, wherein the carrier structure is adapted to or is designed to be adaptable to the implantation location in any direction.

50. The implantable device as set forth in claim 34, wherein the carrier structure comprises twisted wire-like elements which are woven together or interlaced or mutually twisted portions of wire-like elements which are woven through each other at intersection points individually or in the form of twisted elements.

51. The implantable device as set forth in claim 34, wherein the carrier structure is formed from at least one wire-like element in a single-layer, double-layer or multi-layer configuration.

52. The implantable device as set forth in claim 51, wherein the carrier structure is formed of one or more individual layers or strata comprised of the same material.

53. The implantable device as set forth in claim 52, wherein at least one of the layers comprises shape memory material, at least one of the layers comprises polyester and at least one of the layers comprises PTFE.

54. The implantable device as set forth in claim 52, wherein at least one membrane element is arranged between at least two layers of the carrier structure.

55. The implantable device as set forth in claim 51, wherein the carrier structure is formed of one or more individual layers or strata comprised of different materials.

56. The implantable device as set forth in claim 34, further comprising a marker for visually indicating the implantable device under a monitoring apparatus during an implantation procedure.

57. The implantable device as set forth in claim 56, wherein the marker is a micro spiral provided at an edge on the implantable device.

58. The implantable device as set forth in claim 56, wherein the marker comprises an X-ray-visible material containing between 70 and 90% platinum and between 30 and 10% iridium.

\* \* \* \* \*